US007775979B2

(12) United States Patent
Thomenius et al.

(10) Patent No.: US 7,775,979 B2
(45) Date of Patent: Aug. 17, 2010

(54) TRANSMIT AND RECEIVE INTERFACE ARRAY FOR HIGHLY INTEGRATED ULTRASOUND SCANNER

(75) Inventors: Kai E. Thomenius, Clifton Park, NY (US); Robert Gideon Wodnicki, Niskayuna, NY (US); Ye-Ming Li, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 1449 days.

(21) Appl. No.: 11/172,599

(22) Filed: Jun. 29, 2005

(65) Prior Publication Data

US 2007/0016026 A1 Jan. 18, 2007

(51) Int. Cl.
*A61B 8/00* (2006.01)
(52) U.S. Cl. ...................... 600/437; 600/450
(58) Field of Classification Search ................ 600/437, 600/459, 460, 170, 160, 140; 29/25.35; 367/180–182, 367/17, 174, 170, 178
See application file for complete search history.

(56) References Cited

U.S. PATENT DOCUMENTS

| 5,622,177 | A | 4/1997 | Breimesser | 128/662.06 |
|---|---|---|---|---|
| 6,731,151 | B1 | 5/2004 | Doutreloigne | 327/333 |
| 6,759,888 | B1 * | 7/2004 | Wodnicki | 327/382 |
| 7,686,766 | B2 * | 3/2010 | Quistgaard et al. | 600/459 |
| 2005/0154300 | A1 * | 7/2005 | Wodnicki et al. | 600/437 |

OTHER PUBLICATIONS

Doutreloigne et al., "A Versatile Micropower High-Voltage Flat-Panel Display Driver etc." IEEE J. Solid-State Circuits, vol. 36, No. 12, Dec. 2001, pp. 2039-2048.
Wygant et al., "A Miniature Real-Time Volumetric Ultrasound Imaging System," Proc. SPIE, vol. 5750, pp. 26-36, Medical Imaging 2005: Ultrasonic Imaging and Signal Processing, Publ. Date: Apr. 2005.
K.H. Becks, E. Beyne, O. Ehrmann, P. Gerlach, L.M. Gregor, P. Pieters, M. Topper, C. Truzzi and J. Wolf, A MCM-D-type Module for the ATLAS Pixel Detector, 1999 IEEE, pp. 38-41.

* cited by examiner

*Primary Examiner*—Eric F Winakur
*Assistant Examiner*—Lawrence N Laryea
(74) *Attorney, Agent, or Firm*—Fletcher Yoder PC

(57) ABSTRACT

An ultrasonic transducer probe having a highly integrated interface circuit array. Low-voltage transmit control signals from the system are transmitted on the system transmit channels via the ultrasound probe cable and into the interface circuit array. These transmit control signals are routed through the interface circuit array using a dense switching matrix. Once the low-voltage transmit control signals reach individual cells within the interface array, they are decoded and used to control local high-voltage pulser circuits to drive individual ultrasound transducer elements made up of selected subelements that are co-integrated with the interface electronics. The interface cell circuitry further comprises a high-voltage transmit/receive switch, which is closed when the high-voltage pulser is transmitting to protect the low-voltage components.

26 Claims, 21 Drawing Sheets

TRANSMIT AND RECEIVE INTERFACE ARRAY FOR HIGHLY INTEGRATED ULTRASOUND SCANNER

STATEMENT REGARDING FEDERALLY SPONSORED RESEARCH AND DEVELOPMENT

The United States Government may have certain rights in this invention pursuant to U.S. Government Contract Number 1R01 EB002485 awarded by the National Institutes of Health.

BACKGROUND OF THE INVENTION

This invention generally relates to integrated circuitry for use in conjunction with ultrasonic transducer elements. In particular, the invention relates to integrated low-voltage and high-voltage circuitry to be located in the probe handle in an ultrasound imaging system. One specific application for such transmit/receive switches is in medical diagnostic ultrasound imaging systems. Another specific example is for non-destructive evaluation of materials, such as castings, forgings, or pipelines.

For the purposes of this disclosure, "low voltage" means any voltage level that is readily implemented in widely available "standard" semiconductor processes. This could be anywhere from 2.5 to 5 V (for CMOS) up to 25 to 30 V (for BiCMOS). In contrast, "high voltage" means voltage levels that are only accessible if more specialized semiconductor processes and device structures are used (e.g., DMOSFETs, silicon on insulator (SOI), trench isolation, etc.) Therefore any voltage level from about 30 V up to as high as 500 V should be considered to be "high voltage".

A medical ultrasound imaging system forms an image by acquiring individual ultrasound lines (or beams). The lines are adjacent to each other and cover the target area to be imaged. Each line is formed by transmitting an ultrasonic pulse in a particular spatial direction and receiving the reflected echoes from that direction. The spatial characteristics of the transmitted wave and the characteristics of the receive sensitivity determine the quality of the ultrasound image. It is desirable that the ultrasound line gathers target information only from the intended direction and ignores targets at other directions.

Conventional ultrasound imaging systems comprise an array of ultrasonic transducer elements that are used to transmit an ultrasound beam and then receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver may be dynamically focused at a succession of ranges along the scan line as the reflected ultrasonic waves are received.

For ultrasound imaging, the array typically has a multiplicity of transducer elements arranged in one or more rows and driven with separate voltages. By selecting the time delay (or phase) and amplitude of the applied voltages, the individual transducer elements in a given row can be controlled to produce ultrasonic waves that combine to form a net ultrasonic wave that travels along a preferred vector direction and is focused in a selected zone along the beam.

The same principles apply when the transducer probe is employed to receive the reflected sound in a receive mode. The voltages produced at the receiving transducer elements are summed so that the net signal is indicative of the ultrasound reflected from a single focal zone in the object. As with the transmission mode, this focused reception of the ultrasonic energy is achieved by imparting separate time delay (and/or phase shifts) and gains to the signal from each receiving transducer element. The time delays are adjusted with increasing depth of the returned signal to provide dynamic focusing on receive.

The quality or resolution of the image formed is partly a function of the number of transducer elements that respectively constitute the transmit and receive apertures of the transducer array. Accordingly, to achieve high image quality, a large number of transducer elements is desirable for both two- and three-dimensional imaging applications. The ultrasonic transducer elements are typically located in a hand-held transducer probe that is connected by a flexible cable to an electronics unit that processes the transducer signals and generates ultrasound images. The transducer probe may carry both ultrasound transmit circuitry and ultrasound receive circuitry.

It is known to include high-voltage components in the transmit circuitry to drive the individual ultrasonic transducer elements, while low-voltage, high-density digital logic circuitry is used to provide transmit signals to the high-voltage drivers. The high-voltage drivers typically operate at voltages of up to approximately ±100 volts, while the low-voltage logic circuitry has an operating voltage on the order of 5 volts in the case of TTL logic. The high-voltage drivers may be fabricated as discrete components or as integrated circuits, while the low-voltage logic circuitry may be fabricated as a separate integrated circuit or combined with the high-voltage circuitry on a single chip. In addition to transmit circuitry including the high-voltage drivers and low-voltage logic circuitry, the transducer head may include low-noise, low-voltage analog receive circuitry. The low-voltage receive circuitry, like the transmit logic circuitry, typically has an operating voltage on the order of 5 volts, and may be a separate integrated circuit or may be fabricated with the low-voltage transmit logic circuitry as a monolithic integrated circuit.

Typically, a transmit/receive switch is placed between the output-stage transistors and the transducer element. The transmit/receive switch is also connected to the low-voltage receive circuit. The transmit/receive switch has two states. In the transmit state, the transmit/receive switch connects the output-stage transistors to the ultrasonic transducer element, while isolating the receive circuit from the high-voltage transmit pulse. In the receive state, the transmit/receive switch isolates the output-stage transistors from the ultrasonic transducer element and instead connects the receive circuit to the transducer element.

Conventional medical ultrasound imaging creates two-dimensional, cross-sectional images using one-dimensional linear or phased array transducers. These transducers are built with approximately 100 to 200 elements arranged in a linear fashion. The transducer elements are connected to high-voltage pulsers in the system. The pulsers send waveforms to the transducer elements, which in turn convert the electrical waveforms into acoustic waves. By properly controlling the waveforms, a focused sound beam is generated. The signal level of the electrical waveforms can be several hundred volts in order to generate the desired level of acoustic energy. Connecting a few hundred transducer elements to the system is technically feasible with current technology. Current ultrasound systems address the problem of increased channel count by attempting to integrate discrete electronics at the board level. These systems typically are able to drive only about 128-256 channels and consume a large amount of power. Most of this power is expended to drive the cable.

Two-dimensional transducer arrays are required for three-dimensional imaging. These types of transducer arrays typically employ several thousand elements. For proper beamforming, each one of these elements must be connected to a beamforming channel. Connecting several thousand elements to respective pulsers in the system is technically not feasible because a cable bundle of coaxial or other wire comprising a sufficient number of conductors for several thousand elements would be too thick and heavy to be ergonomically viable. Also, a cable that would connect the system pulsers to the transducer elements would present a very large capacitance load compared to the impedance of the two-dimensional array element. Therefore, a majority of the pulser current would be drawn into the cable capacitance while only a small fraction of the current would remain for the transducer element. As a result, only a small fraction of the energy supplied by the pulser would be converted to acoustic waves. Consequently, much more power would have to be supplied by the pulser circuitry than would be required from a linear array. This additional power requirement might be tolerable for a full-size clinical ultrasound scanner. However, it would be prohibitive for a portable system, which would not be able to supply sufficient cooling for the pulsers. In addition, the portable system would suffer drastically reduced battery life.

U.S. patent application Ser. No. 10/697,518, filed on Oct. 30, 2003, discloses the concept of integrating pulsers directly in the probe handle. This solves the problem of power consumption due to the cable, but does not address the more pragmatic concerns about the amount of power expended by the actual pulser control architecture. In addition, this patent application does not address the actual architecture of the pulser control circuit and does not treat the transmit/receive circuit.

There is a need to solve the problem of driving a large number of small ultrasound transducers in a two-dimensional array configuration with minimal power expenditure and in a small footprint.

BRIEF DESCRIPTION OF THE INVENTION

The invention is directed to an ultrasonic transducer probe having a highly integrated interface circuit array. Low-voltage transmit control signals from the system are transmitted on the system transmit channels via the ultrasound probe cable and into the interface circuit array. These transmit control signals are routed through the interface circuit array using a dense switching matrix. Once the low-voltage transmit control signals reach individual cells within the interface array, they are decoded and used to control local high-voltage pulser circuits to drive individual ultrasound transducer elements made up of selected subelements that are co-integrated with the interface electronics. The interface cell circuitry further comprises a high-voltage transmit/receive switch, which is closed when the high-voltage pulser is transmitting to protect the low-voltage components.

One aspect of the invention is a device comprising a multiplicity of ultrasonic transducers and a multiplicity of interface circuit cells, each of the ultrasonic transducers being electrically coupled to a respective one of the interface circuit cells, and each of the interface circuit cells comprising a high-voltage pulser for driving a respective ultrasonic transducer, a low-voltage switch for providing pulser control signals when the low-voltage switch is on, a low-voltage digital control circuit that outputs switch state control signals for controlling the state of the low-voltage switch, and a high-voltage transmit/receive switch disposed between the low-voltage switch and the respective ultrasonic transducer for providing a path for receive signals from the respective ultrasonic transducer to the low-voltage switch when the transmit/receive switch is on, wherein the transmit/receive switch blocks the pulser output from reaching the low-voltage switch via the path when the transmit/receive switch is off.

Another aspect of the invention is a probe comprising: a multiplicity of ultrasonic transducers; a multiplicity of high-voltage pulsers coupled for respectively driving the transducers in accordance with low-voltage pulser control signals inputted to the probe in a transmit mode; and a multiplicity of high-voltage transmit/receive switches, each of the high-voltage transmit/receive switches having an input electrically connected to a junction at an electrical connection between a respective high-voltage pulser and a respective ultrasonic transducer and having an output, any signal at the input being passed to the output in a receive mode and being not passed to the output in the transmit mode.

A further aspect of the invention is an integrated device comprising a multiplicity of ultrasonic transducers arranged along a first set of generally parallel lines in a first stratum; a multiplicity of interface circuit cells arranged along a second set of generally parallel lines in a second stratum; and a multiplicity of electrical connections, each of the electrical connections electrically connecting a respective one of the interface circuit cells to a respective ultrasonic transducer, wherein each of the interface circuit cells comprises: a high-voltage pulser for driving the respective ultrasonic transducer, a low-voltage switch for providing pulser control signals when the low-voltage switch is on, a low-voltage digital control circuit that outputs switch state control signals for controlling the state of the low-voltage switch, and a high-voltage transmit/receive switch disposed between the low-voltage switch and the respective ultrasonic transducer for providing a path for receive signals from the respective ultrasonic transducer to the low-voltage switch when the transmit/receive switch is on, wherein the transmit/receive switch blocks the pulser output from reaching the low-voltage switch via the path when the transmit/receive switch is off.

Yet another aspect of the invention is an ultrasound transducer array comprising a multiplicity of ultrasound transducers, a multiplicity of interface circuit cells, and a multiplicity of output nodes, each interface circuit cell being electrically connected to a respective one of the ultrasound transducers via a respective one of the output nodes, wherein each of the interface circuit cells comprises: a high-voltage pulser for driving the respective ultrasound transducer, a low-voltage switch for providing pulser control signals when the low-voltage switch is on, a low-voltage digital control circuit that outputs switch state control signals for controlling the state of the low-voltage switch, and a high-voltage transmit/receive switch disposed between the low-voltage switch and the respective ultrasound transducer for providing a path for receive signals from the respective ultrasound transducer to the low-voltage switch when the transmit/receive switch is on, wherein the transmit/receive switch blocks the pulser output from reaching the low-voltage switch via the path when the transmit/receive switch is off.

A further aspect of the invention is an ultrasound transducer probe comprising a plurality of integrated devices tiled together in two rows, wherein each of the integrated devices has four sides and comprises: a multiplicity of ultrasonic transducers arranged along a first set of generally parallel lines disposed in an area of a first stratum; a multiplicity of interface circuit cells arranged along a second set of generally parallel lines disposed in a first area of a second stratum that underlies the area of the first stratum; a first multiplicity of electrical connections, each of the electrical connections of the first multiplicity electrically connecting a respective one of the interface circuit cells to a respective ultrasonic transducer; a multiplicity of pads disposed in a second area of the second stratum that does not overlap with the first area of the second stratum and extends along a marginal area extending along one of the four sides; and a second multiplicity of electrical connections, each of the electrical connections of the second multiplicity electrically connecting a respective one of the interface circuit cells to a respective pad. Each of the interface circuit cells comprises: a high-voltage pulser for driving the respective ultrasonic transducer, a low-voltage switch for providing pulser control signals when the switch is on, a low-voltage digital control circuit that outputs switch state control signals for controlling the state of the low-voltage switch, and a high-voltage transmit/receive switch disposed between the low-voltage switch and the respective ultrasonic transducer for providing a path for receive signals from the respective ultrasonic transducer to the low-voltage switch when the transmit/receive switch is on, wherein the transmit/receive switch blocks the pulser output from reaching the low-voltage switch via the path when the transmit/receive switch is off.

Other aspects of the invention are disclosed and claimed below.

BRIEF DESCRIPTION OF THE DRAWINGS

Reference will now be made to the drawings in which similar elements in different drawings bear the same reference numerals.

DETAILED DESCRIPTION OF THE INVENTION

Recently semiconductor processes have been used to manufacture ultrasonic transducers of a type known as micromachined ultrasonic transducers (MUTs), which may be of the capacitive (cMUT) or piezoelectric (pMUT) variety. MUTs are tiny diaphragm-like devices with electrodes that convert the sound vibration of a received ultrasound signal into a modulated capacitance. For transmission the capacitive charge is modulated to vibrate the diaphragm of the device and thereby transmit a sound wave. One advantage of MUTs is that they can be made using semiconductor fabrication processes, such as microfabrication processes grouped under the heading "micromachining". The systems resulting from such micromachining processes are typically referred to as "micromachined electro-mechanical systems" (MEMS). As explained in U.S. Pat. No. 6,359,367:

> Micromachining is the formation of microscopic structures using a combination or subset of (A) Patterning tools (generally lithography such as projection-aligners or wafer-steppers), and (B) Deposition tools such as PVD (physical vapor deposition), CVD (chemical vapor deposition), LPCVD (low-pressure chemical vapor deposition), PECVD (plasma chemical vapor deposition), and (C) Etching tools such as wet-chemical etching, plasma-etching, ion-milling, sputter-etching or laser-etching. Micromachining is typically performed on substrates or wafers made of silicon, glass, sapphire or ceramic. Such substrates or wafers are generally very flat and smooth and have lateral dimensions in inches. They are usually processed as groups in cassettes as they travel from process tool to process tool. Each substrate can advantageously (but not necessarily) incorporate numerous copies of the product. There are two generic types of micromachining . . . 1) Bulk micromachining wherein the wafer or substrate has large portions of its thickness sculptured, and 2) Surface micromachining wherein the sculpturing is generally limited to the surface, and particularly to thin deposited films on the surface. The micromachining definition used herein includes the use of conventional or known micromachinable materials including silicon, sapphire, glass materials of all types, polymers (such as polyimide), polysilicon, silicon nitride, silicon oxynitride, thin film metals such as aluminum alloys, copper alloys and tungsten, spin-on-glasses (SOGs), implantable or diffused dopants and grown films such as silicon oxides and nitrides.

The same definition of micromachining is adopted herein.

For purposes of illustration, various embodiments of the invention will be described in the context of an array comprising capacitive micromachined ultrasonic transducers (cMUTs). However, it should be understood that the aspects of the invention disclosed herein are not limited in their application to cMUT arrays, but rather may also be applied to arrays that employ pMUTs or PZT elements.

Figure 1:
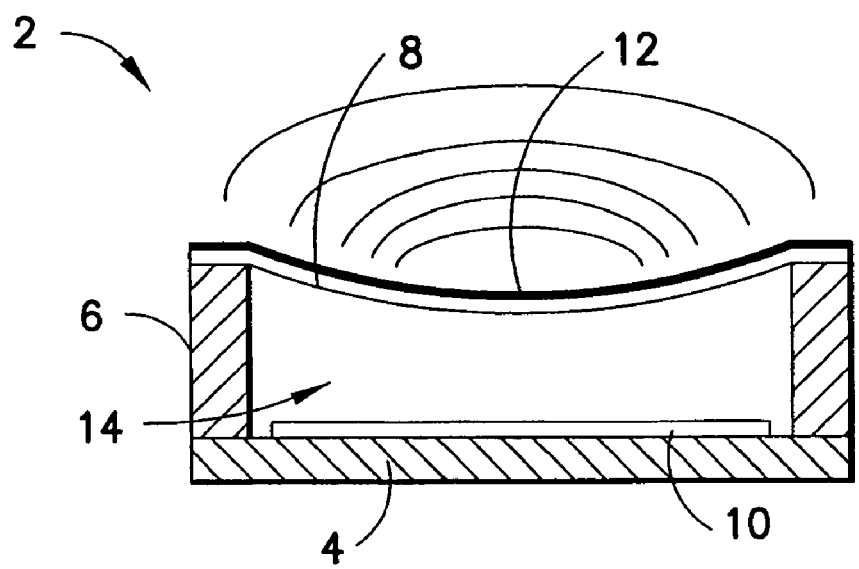
FIG. 1 is a drawing showing a cross-sectional view of a typical cMUT cell.

Referring to FIG. 1, a typical cMUT transducer cell 2 is shown in cross section. An array of such cMUT transducer cells is typically fabricated on a substrate 4, such as a heavily doped silicon (hence, semiconductive) wafer. For each cMUT transducer cell, a thin membrane or diaphragm 8, which may be made of silicon nitride, is suspended above the substrate 4. The membrane 8 is supported on its periphery by an insulating support 6, which may be made of silicon oxide or silicon nitride. The cavity 14 between the membrane 8 and the substrate 4 may be air- or gas-filled or wholly or partially evacuated. Typically, cMUTs are evacuated as completely as the processes allow. A film or layer of conductive material, such as aluminum alloy or other suitable conductive material, forms an electrode 12 on the membrane 8, and another film or layer made of conductive material forms an electrode 10 on the substrate 4. Alternatively, the bottom electrode can be formed by appropriate doping of the semiconductive substrate 4.

The two electrodes 10 and 12, separated by the cavity 14, form a capacitance. When an impinging acoustic signal causes the membrane 8 to vibrate, the variation in the capacitance can be detected using associated electronics (not shown in FIG. 1), thereby transducing the acoustic signal into an electrical signal. Conversely, an AC signal applied to one of the electrodes will modulate the charge on the electrode, which in turn causes a modulation in the capacitive force between the electrodes, the latter causing the diaphragm to move and thereby transmit an acoustic signal.

The individual cells can have round, rectangular, hexagonal, or other peripheral shapes. Hexagonal shapes provide dense packing of the cMUT cells of a transducer subelement. The cMUT cells can have different dimensions so that the transducer subelement will have composite characteristics of the different cell sizes, giving the transducer a broadband characteristic.

It is difficult to produce electronics that would allow individual control over such small cells. While in terms of the acoustical performance of the array as a whole, the small cell size is excellent and leads to great flexibility, control is limited to larger structures. Grouping together multiple cells and connecting them electrically allows one to create a larger subelement, which can have the individual control while maintaining the desired acoustical response. One can form rings or other elements by connecting subelements together using a switching network. The elements can be reconfigured by changing the state of the switching network to interconnect different subelements to each other. However, individual subelements cannot be reconfigured to form different subelements.

MUT cells can be connected together (i.e., without intervening switches) in the micromachining process to form what will, in this specification, be referred to as an "acoustical subelement". These acoustical subelements (or acoustical subelements not comprising interconnected MUT cells) will be interconnected by microelectronic switches to form larger elements by placing such switches within the silicon layer or on a different substrate situated directly adjacent to the transducer array. This construction is based on semiconductor processes that can be done with low cost in high volume.

In general, an acoustical subelement is a single cell or a group of electrically connected cells that cannot be reconfigured, i.e., the acoustical subelement is the smallest independently controlled acoustical unit. The term "subelement" (without the qualifier "acoustical"), as used herein, means an acoustical subelement and its associated integrated electronics. An "element" is formed by connecting acoustic subelements together using a switching network. The elements can be reconfigured by changing the state of the switching network. At least some of the switches included in the switching network are part of the associated integrated electronics.

Figure 2:
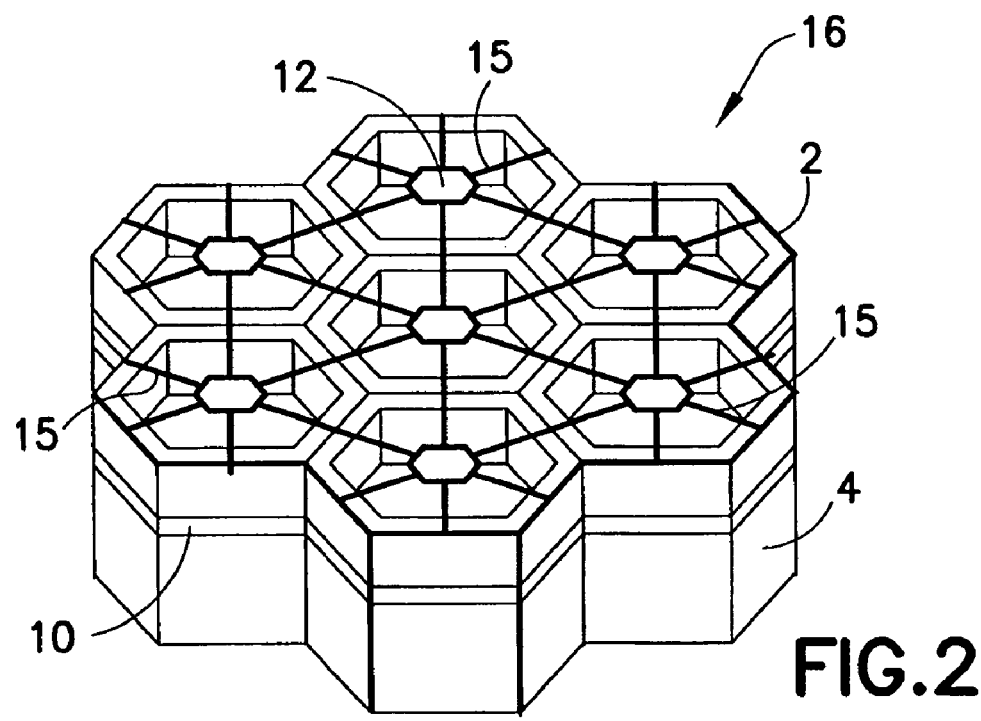
FIG. 2 is a drawing showing a "daisy" subelement formed from seven hexagonal MUT cells having their top and bottom electrodes respectively connected together without intervening switches.

For the purpose of illustration, FIG. 2 shows a "daisy" acoustical subelement 16 made up of seven hexagonal cMUT cells 2: a central cell surrounded by a ring of six cells, each cell in the ring being contiguous with a respective side of the central cell and the adjoining cells in the ring. The top electrodes 12 of each cMUT cell 2 are electrically coupled together by connections that are not switchably disconnectable. In the case of a hexagonal array, six conductors 15 radiate outward from the top electrode 12 like "spokes" and are respectively connected to the top electrodes of the neighboring cMUT cells (except in the case of cells on the periphery, which connect to three, not six, other cells). Similarly, the bottom electrodes 10 of each cell 2 are electrically coupled together by connections that are not switchably disconnectable, forming a seven-times-larger acoustical subelement 16.

Acoustical subelements of the type seen in FIG. 2 can be arranged to form a two-dimensional array on a semiconductive (e.g., silicon) substrate. These acoustical subelements can be reconfigured to form elements, such as annular rings, using a switching network. Reconfigurability using silicon-based ultrasound transducer subelements is described in U.S. Pat. No. 6,865,140. One form of reconfigurability is the mosaic annular array, also described in that patent. The mosaic annular array concept involves building annular elements by grouping acoustical subelements together using a reconfigurable electronic switching network. The reconfigurability can be used to step the beam along the larger underlying two-dimensional transducer array in order to form a scan or image.

Most apertures will consist of contiguous grouped subelements interconnected to form a single larger element. In this case, it is not necessary to connect every subelement directly to its respective bus line. It is sufficient to connect a limited number of subelements within a given group and then connect the remaining subelements to each other. In this way the transmit signal is propagated from the system along the bus lines and into the element along a limited number of access points. From there the signal spreads within the element through local connections.

Given a particular geometry, the reconfigurable array maps acoustical subelements to system channels. This mapping is designed to provide improved performance. The mapping is done through a switching network, which is ideally placed directly in the substrate upon which the cMUT cells are constructed, but can also be in a different substrate integrated adjacent to the transducer substrate. Since cMUT arrays are built directly on top of a silicon substrate, the switching electronics can be incorporated into that substrate.

Figure 3:
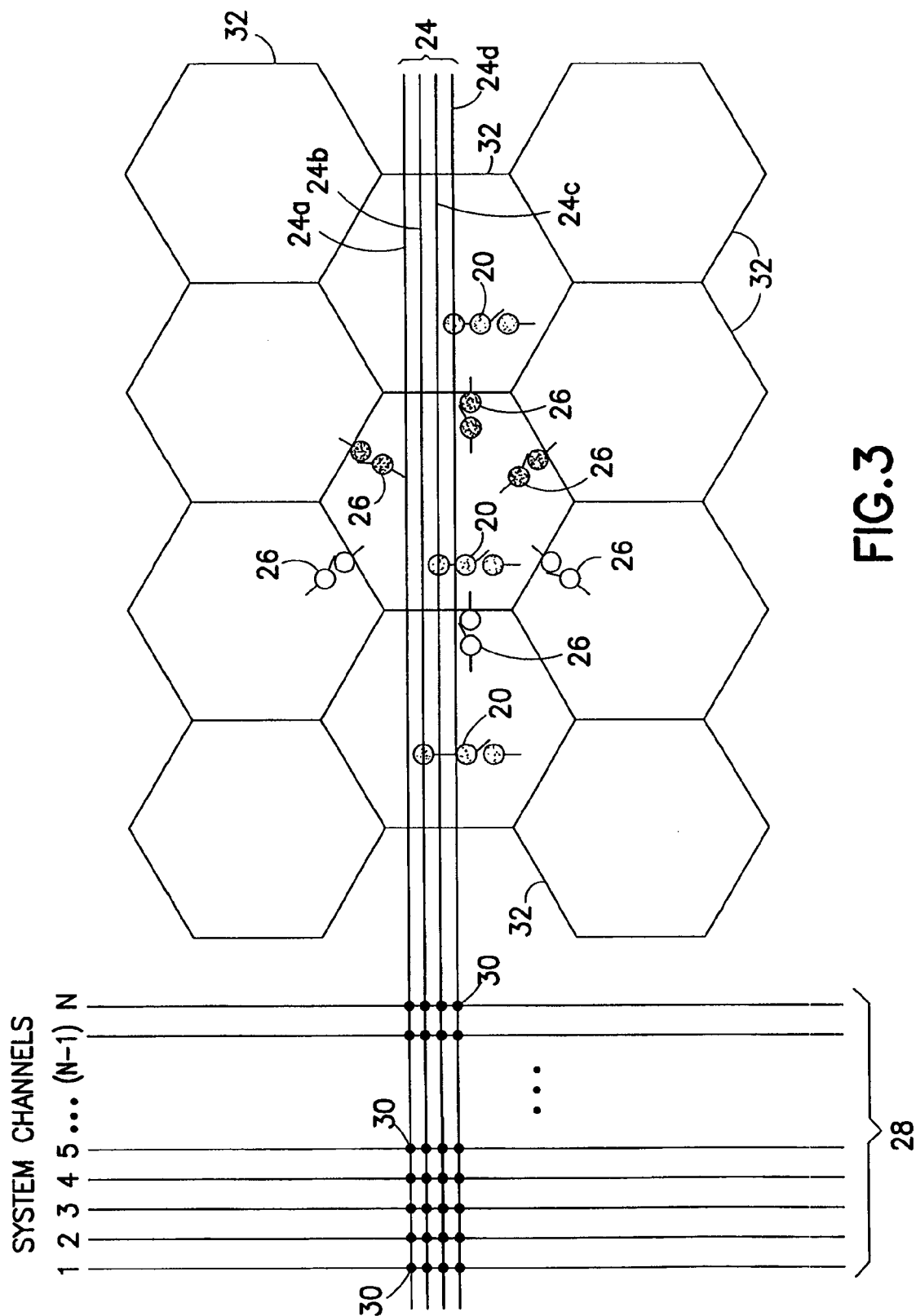
FIG. 3 is a drawing showing an architecture that allows a particular subelement in a particular row of a cMUT array to be connected to any one of a multiplicity of system channel bus lines.

One implementation of a reconfigurable cMUT array is shown in FIG. 3. Here an access switch 20 is used to connect a given acoustical subelement 32 to a row bus line of bus 24. This architecture is directly applicable to a mosaic annular array. In such a device multiple rings can be formed using the present architecture, wherein each ring is connected to a single system channel using one or more access switches, each of which is connected to a bus line, which is in turn connected to a system channel. The access switches are staggered as shown in FIG. 3 to reduce the number required for a given number of bus lines. The row bus lines are connected to the system channels using a cross-point switching matrix as shown in FIG. 3.

The number of access switches and row bus lines is determined by the size constraints and the application. For the purpose of disclosing one exemplary non-limiting implementation (shown in FIG. 3), a single access switch 20 for each acoustical subelement 32 and four row bus lines 24a-24d for each row of the array will be assumed. The second type of switch is a matrix switch 26, which is used to connect a connection point of one subelement to the connection point of a neighboring subelement. The connection point connects the acoustic subelement or transducer 32 to the access switch 20 for that subelement, to the three matrix switches 26 associated with that subelement, and to the three matrix switches associated with three neighboring subelements. A signal that travels through a matrix switch gets connected to the common connection point of the neighboring subelement. This allows an acoustical subelement 32 to be connected to a system channel through the integrated electronics associated with a neighboring acoustical subelement. This also means that an acoustical subelement may be connected to a system channel even though it is not directly connected via an access switch. While FIG. 3 shows three matrix switches 26 per subelement, it is also possible to have fewer than three to conserve area or to allow for switches which have lower on resistance and therefore have larger area. In addition, matrix switches can be used to route around a known bad subelement for a given array. Finally, while hexagonal subelements are shown, columnar or rectangular subelements are also possible and these might require fewer switches.

FIG. 3 depicts how the switching network might work for a particular subelement. This is only an exemplary arrangement. A bus 24, which contains four row bus lines 24a through 24d, runs down the row of acoustical subelements 32. FIG. 3 shows only three subelements in this row, but it should be understood that other subelements in this row are not shown. The row bus lines of bus 24 are multiplexed to system channel bus lines of system channel bus 38 at the end of a row by means of multiplexing switches 40, which form a cross-point switching matrix. As seen in FIG. 3, each row bus line 24a-24d can be connected to any one of the system channel bus lines of bus 38 by turning on the appropriate multiplexing switch 40 and turning off the multiplexing switches that connect the particular row bus line to the other system channel bus lines. These multiplexing electronics can be off to the side and thus are not as restricted by size. FIG. 3 shows a fully populated cross-point switching matrix. However, in cases wherein it is not necessary to have switches that allow every bus line to be connected to every system channel, a sparse cross-point switching matrix can be used in which only a small subset of the system channels can be connected to a given bus line, in which case only some of switches 40 depicted in FIG. 3 would be present.

An access switch is so named because it gives a subelement direct access to a bus line. In the exemplary implementation depicted in FIG. 3, there are six other switch connections for each subelement. These connections take the form of matrix switches 26. A matrix switch allows a subelement to be connected to a neighboring subelement. While there are six connections to neighboring subelements for each subelement in this hexagonal pattern, only three switches reside in each subelement while the other three connections are controlled by switches in the neighboring subelements. Thus there is a total of four switches and associated digital addressing and control logic (not shown) in each subelement. This is just one exemplary implementation. The number of bus lines, the number of access switches, and the number and topology of the matrix switches could all be different, but the general concept would remain. Although the access and matrix switches can be separately packaged components, it is possible to fabricate the switches within the same semiconductor substrate on which the MUT array is to be fabricated.

U.S. patent application Ser. No. 10/697,518, entitled "Methods and Apparatus for Transducer Probe", discloses the concept of integrating high-voltage pulsers into the handle of an ultrasound transducer probe and then activating those pulsers using timing signals that pass through a low-voltage switching matrix (e.g., a multiplexer), also incorporated in the probe. The present invention builds upon that concept.

Figure 4:
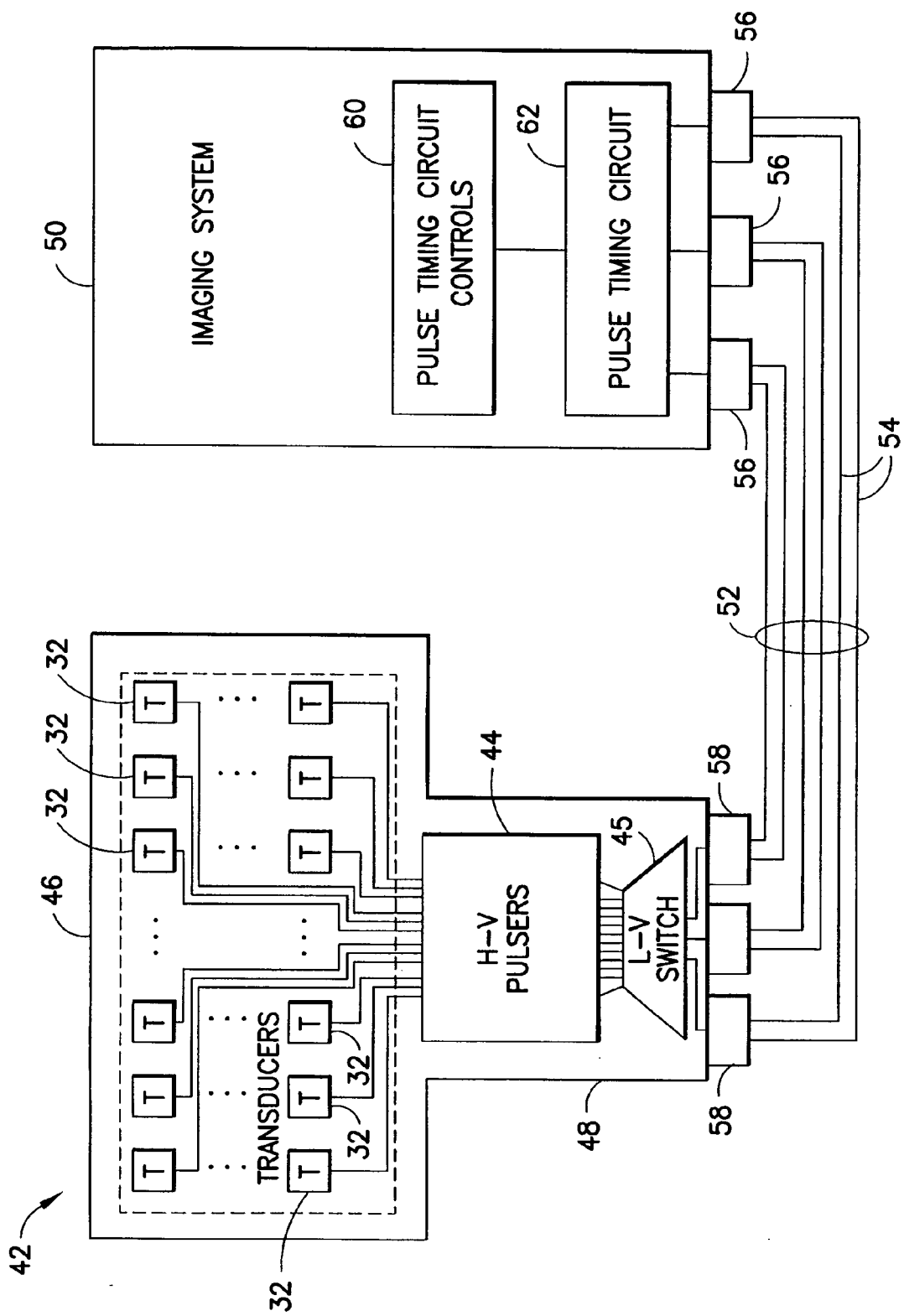
FIG. 4 is a block diagram representing portions of a transducer probe connected to an imaging system via cables in accordance with one embodiment of the present invention, the probe comprising a low-voltage switching matrix that receives pulse timing signals and a multiplicity of high-voltage pulsers that are activated in accordance with those timing signals.

In accordance with one embodiment of the present invention shown in FIG. 4, an ultrasonic probe 42 comprises a multiplicity of acoustical subelements (i.e., transducers) 32 and a corresponding multiplicity of high-voltage pulsers 44 (one pulser circuit per acoustical subelement) which are respectively disposed in the probe head 46 and the probe handle 48. The probe 42 is connected to an ultrasound imaging system 50 by means of one or more cables 52 comprising a multiplicity of electrical conductors 54. Each cable 52 is coupled to the imaging system 50 and to the probe 42 by respective cable connectors 56 and 58. The pulsers receive pulse timing signals via a low-voltage switching matrix 45 (also incorporated in the probe handle 48).

In various configurations, the pulsers may comprise unipolar, bipolar, or multi-level pulsers, or a combination thereof. Placing the pulsers in the probe handle 48 advantageously permits pulse timing circuitry 62 (controlled by pulse timing control circuitry 60) to be located either in the imaging system 20, as shown in FIG. 4, or in the probe handle (not shown). During transmit, each acoustical subelement 32 making up the transmit aperture receives a respective pulse train. Parameters of the respective pulse train in each channel are varied to achieve focused ultrasound beam transmission. The pulse timing circuit 62 generates multiple low-voltage transmit control (i.e., timing) signals that are carried by the coaxial cables 52 from the imaging system 50 to the probe 42. When the timing signals reach probe handle 48, they are routed to individual pulsers 44 via the low-voltage switching matrix 45, which is reprogrammed before each transmit operation. Routing of signals is such that all subelements that are part of a given transmit element are connected together to receive the same low-voltage transmit control signal. Similarly all subelements that are part of a given receive element are connected together such that their receive signals contribute to the net receive signal for that element.

In accordance with embodiments disclosed herein, there is a one-to-one correspondence of high-voltage pulsers to acoustical subelements. The low-voltage transmit control signals are routed through the switching matrix. Once the low-voltage transmit control signals reach an individual subelement or cell, they are decoded and used to control the local high-voltage pulsers to drive individual acoustical subelements.

In accordance with various embodiments of the present invention disclosed below, an ultrasonic transducer device comprises a multiplicity of ultrasonic transducers and a multiplicity of electronics cells incorporated in a probe, each electronic cell being designed to interface a respective ultrasonic transducer to the imaging system to which the probe is connected via cables. An electronics cell that facilitates, in the alternative, the sending of pulses to a respective ultrasonic transducer during transmission and the receiving of echo signals from the respective ultrasonic transducer during reception will be referred to hereinafter as an "interface circuit cell".

Figure 5:
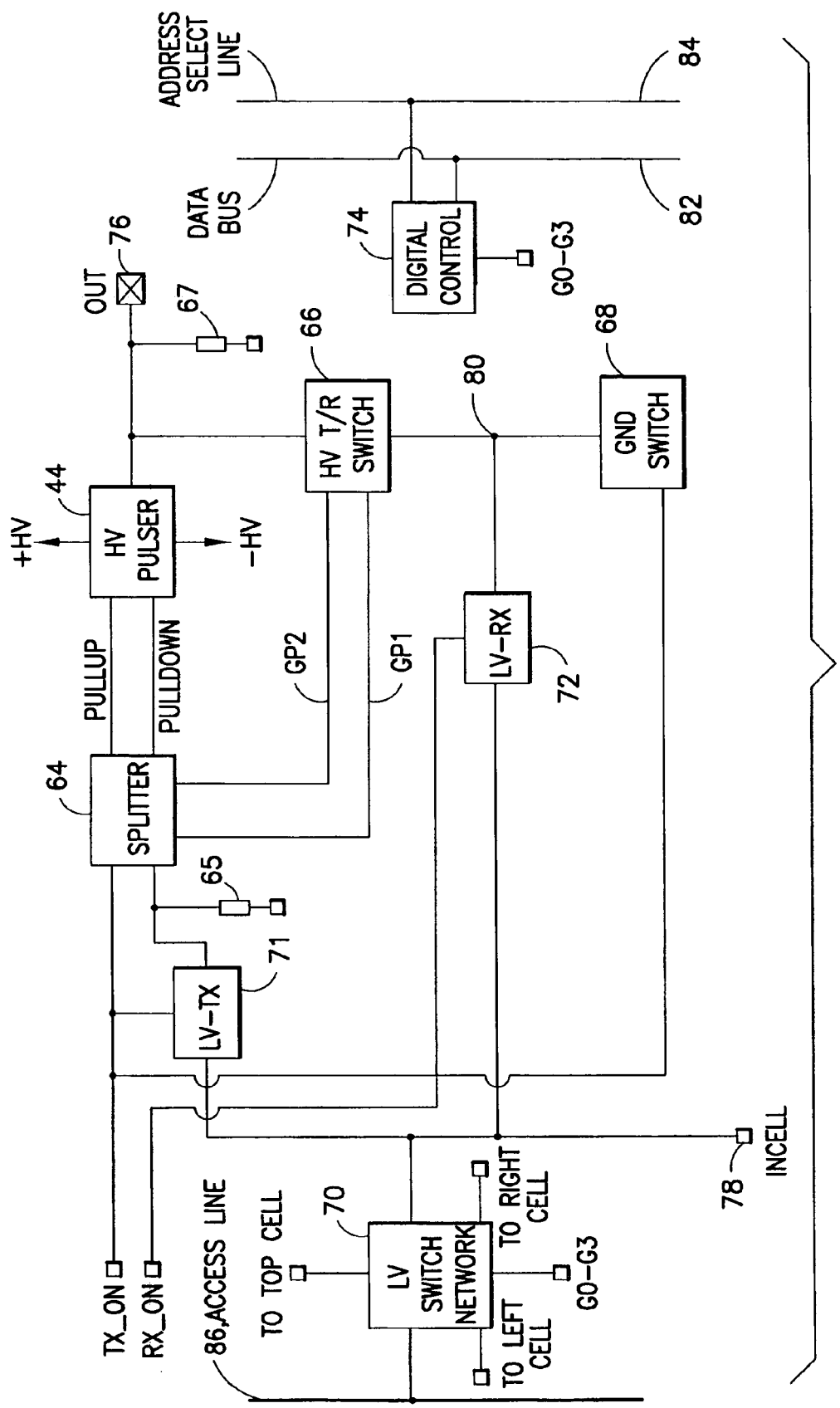
FIG. 5 is a block diagram showing an interface array unit cell architecture in accordance with one embodiment of the present invention. The outputs G0-G3 of the digital control block are the inputs G0-G3 to the low-voltage switch network.

FIG. 5 shows a block level representation of an individual interface circuit cell in accordance with one embodiment of the invention. Each interface circuit cell comprises a high-voltage pulser 44, a low-voltage switching network 70, a low-voltage splitter 64, a high-voltage T/R switch 66, a low-voltage ground switch 68, a low-voltage transmit switch 71, a low-voltage receive switch 72, and a low-voltage digital control circuit 74, connected as shown in FIG. 5. The low-voltage receive switch 72 (labeled LV_RX in FIG. 5) is situated between the center node 78 and the T/R switch 66; the low-voltage transmit switch 71 (labeled LV_TX in FIG. 5) is situated between the center node 78 and the splitter 64.

The interface circuit cell is placed in a transmit mode upon receipt of a global transmit mode control signal at node TX_ON (see transition from low to high level in FIG. 6) from the imaging system. This global transmit mode control signal TX_ON is received by splitter 64, ground switch 68, and low-voltage transmit switch 71. RX_ON is the inverse of TX_ON and is used to control the low-voltage receive switch.

The low-voltage switch network 70 consists of one access switch and three matrix switches, as previously described with reference to FIG. 3. These switches do not have to withstand high voltage and so can be much smaller than equivalent-on-resistance high-voltage switches. During transmit, pulser timing or control signals (e.g., ±3.3 V; see FIG. 6) from the system are sent to the low-voltage switch network 70. The pulser control signals may be sent directly via the access line 86 and the access switch incorporated in switching network 70 of the cell depicted in FIG. 5; or via the access line of a different cell and a matrix switch incorporated in switching network 70 of the cell depicted in FIG. 5; or via the access line of a different cell and a matrix switch incorporated in the switching network of a cell adjacent to cell depicted in FIG. 5. The digital control circuitry 74 stores the states of the access and matrix switches.

Figure 6:
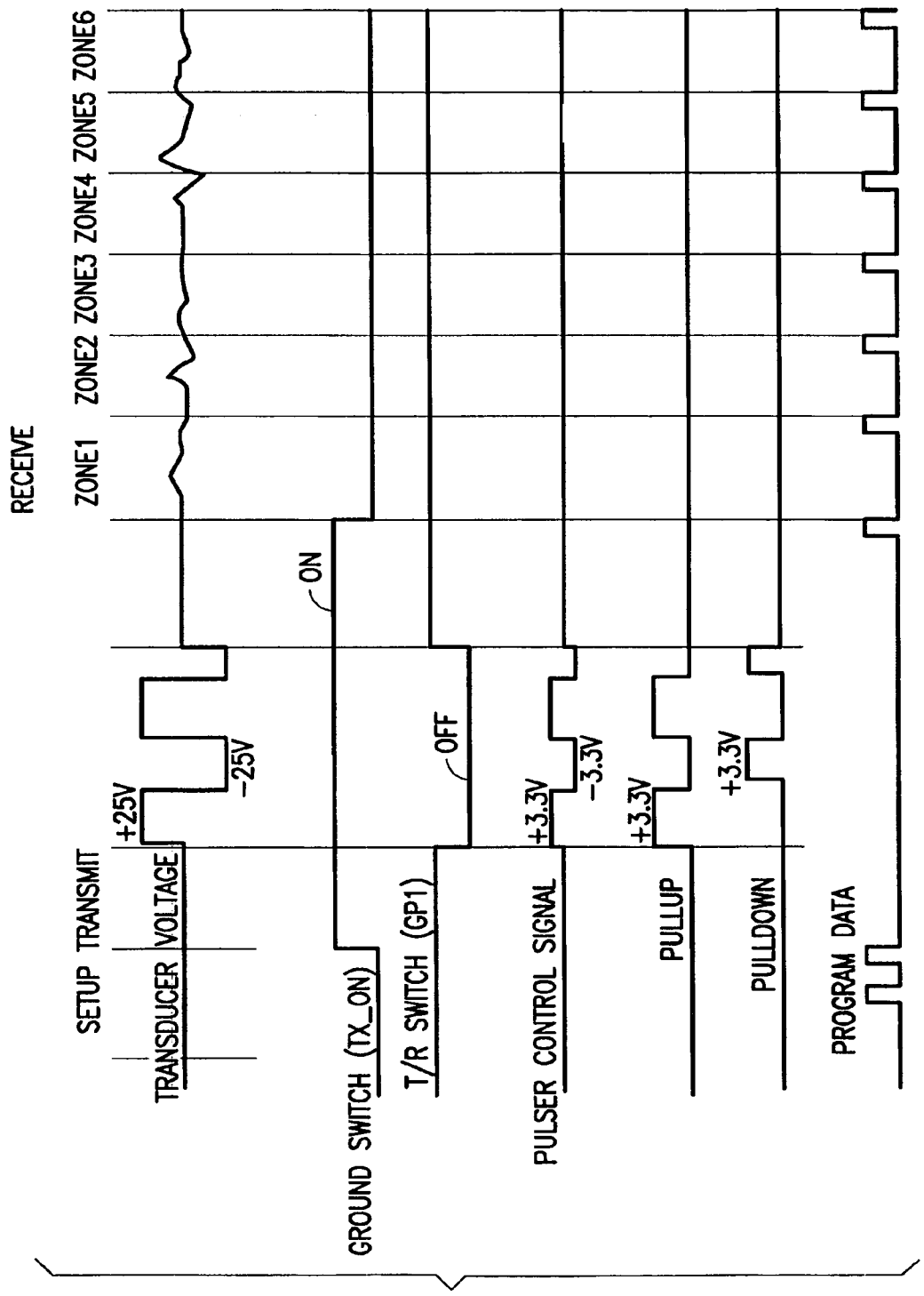
FIG. 6 is a timing diagram showing certain aspects of the operation of the circuitry depicted in FIG. 5, including the timing of pulses input to the ground switch, T/R switch, splitter and pulser and the transducer voltage during transmit and receive.

On transmit, the splitter 64 receives the pulser control signals from the system (via the switching network 70 and the low-voltage transmit switch 71) in the form of low-voltage bipolar pulses (see FIG. 6). The circuit element 65 (which may be, e.g., a resistor or a transmission gate connected to ground) maintains the input of the splitter at a known value, namely ground. This function could also be performed using an analog switch to ground that is controlled by RX_ON. Use of such a low-voltage switch would greatly reduce the amount of area for this function. The splitter 64 splits each bipolar input pulse sequence into two unipolar pulse sequences that are output (see PULLUP and PULLDOWN in FIG. 6) to control the high-voltage pulser 44. The splitter circuitry is shown in detail in FIG. 10 (discussed below).

The high-voltage pulser 44 is located between the splitter 64 and the output node (i.e., signal pad) 76 as illustrated in FIG. 5. The output node 76 is in turn connected to an acoustical subelement (32 in FIG. 4). The pulser drives the output node and its load between +25 V and −25 V (see uppermost waveform in FIG. 6). The pulser 44 drives the output node 76 and its load as a function of the PULLUP and PULLDOWN pulse sequences. The circuit element 67 (which may be, e.g., a resistor or a transmission gate connected to ground) biases the transducer (i.e., the acoustical subelement).

In addition, two other outputs (GP1, GP2) of the splitter 64 carry control signals for the high-voltage T/R switch 66. The high-voltage T/R switch 66 is located between the output node 76 and the low-voltage receive switch 72, as shown in FIG. 5. The purpose of T/R switch 66 is to protect the low-voltage circuitry from the pulser output, which is high voltage during the transmit cycle. During transmit, the T/R switch 66 is turned off and it blocks the transmit voltage from affecting the low-voltage circuitry.

The ground switch 68 is a low-voltage analog transmission gate that is used between the high-voltage T/R switch 66 and ground. During transmit, the ground switch 68 is kept on (see FIG. 6) to hold the receive channel at a preset level. Also the low-voltage receive switch 72 is turned off (via line RX_ON in FIG. 5) during the transmit cycle. The low-voltage receive switch 72 prevents the ground switch 68 from affecting the low-voltage transmit control signal. Whenever the low-voltage transmit control sequence returns to zero, the splitter 64 outputs control signals GP1 and GP2 to cause the T/R switch 66 to be turned on. This action allows the output node 76 to discharge either from a high state or a low state to the ground level.

Once the transmit cycle is finished, the global control signal TX_ON changes level (from high to low, as seen in FIG. 6), causing all of the ground switches to be turned off, which allows the receive channels in all cells to float in preparation for the receive cycle. In the receive cycle, all of the high-voltage T/R switches in the array are turned on. In addition, the low-voltage transmit switch 71 is turned off and low-voltage receive switch 72 is turned on. This allows the low-voltage receive signals from the transducers to be routed to the low-voltage switching network 70, but prevents them from affecting the splitter. The low-voltage switching network 70 routes the signals back to the system on the same channels that were previously used to drive the low-voltage transmit control signals. Once the receive cycle is completed, the array is reconfigured for the next transmit cycle.

The low-voltage circuits in the interface circuit cell shown in FIG. 5 operate around ground; however, the substrate is biased at −25 V due to the pulser operating between +25 V and −25 V. Therefore, the low-voltage circuits must sit in their own wells, which float up around ground. In one proposed design, there are three such wells, respectively biased at +3.0 V, at −3.0 V and at 0 V, respectively represented as DVDD, DVSS and GND in FIGS. 7-12 (described below). The second and third wells sit inside of the well biased at +3.0 V. All of these wells must be properly contacted to their respective supplies to ensure that the circuit operates correctly.

Figure 7:
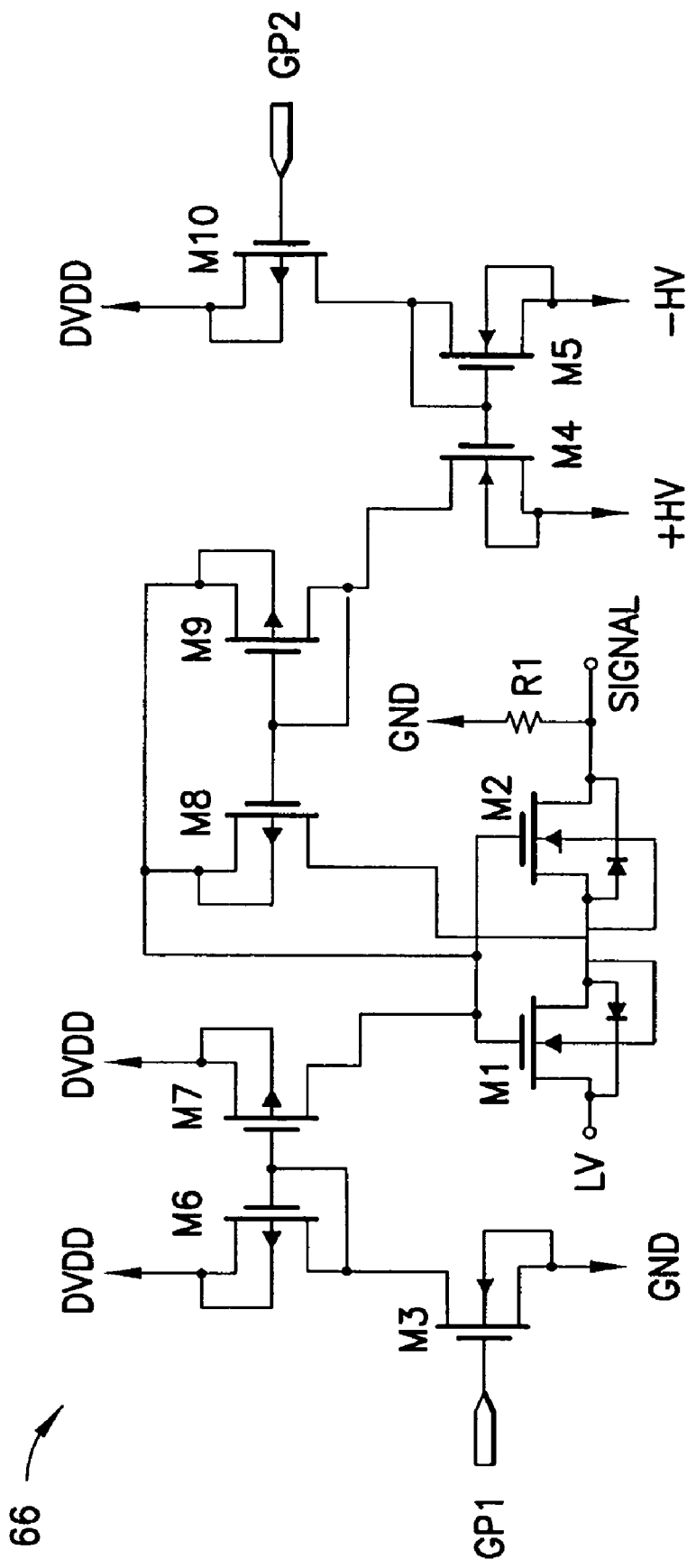
FIG. 7 is a circuit diagram showing a circuit implementation of the high-voltage T/R switch incorporated in the unit cell architecture shown in FIG. 5.

One implementation of the circuitry of the high-voltage T/R switch 66 is shown in FIG. 7. The circuitry of the T/R switch and associated switch control circuitry comprises ten field effect transistors (FETS) M1 through M10 connected as shown. FETs M1 and M2 form the actual high-voltage transmit/receive switch, while FETs M3 through M10 form the T/R switch control circuit. There is a single resistor R1 that is designed to maintain a bias voltage (in this case ground) on the signal pad. Control of the T/R switch is provided by digital signals GP1 and GP2 that are generated by the splitter 64. More specifically, the gates of FETs M3 and M10 respectively receive T/R switch state control signals GP1 and GP2 from the splitter. The operation of this circuit is further detailed in U.S. Pat. No. 6,759,888. The circuit may be further simplified as shown in FIG. 5 of that patent. Here a single FET is used to both turn on and turn off the DMOS FETs and thereby greatly reduces the size of the control circuitry for the T/R switch.

Figure 8:
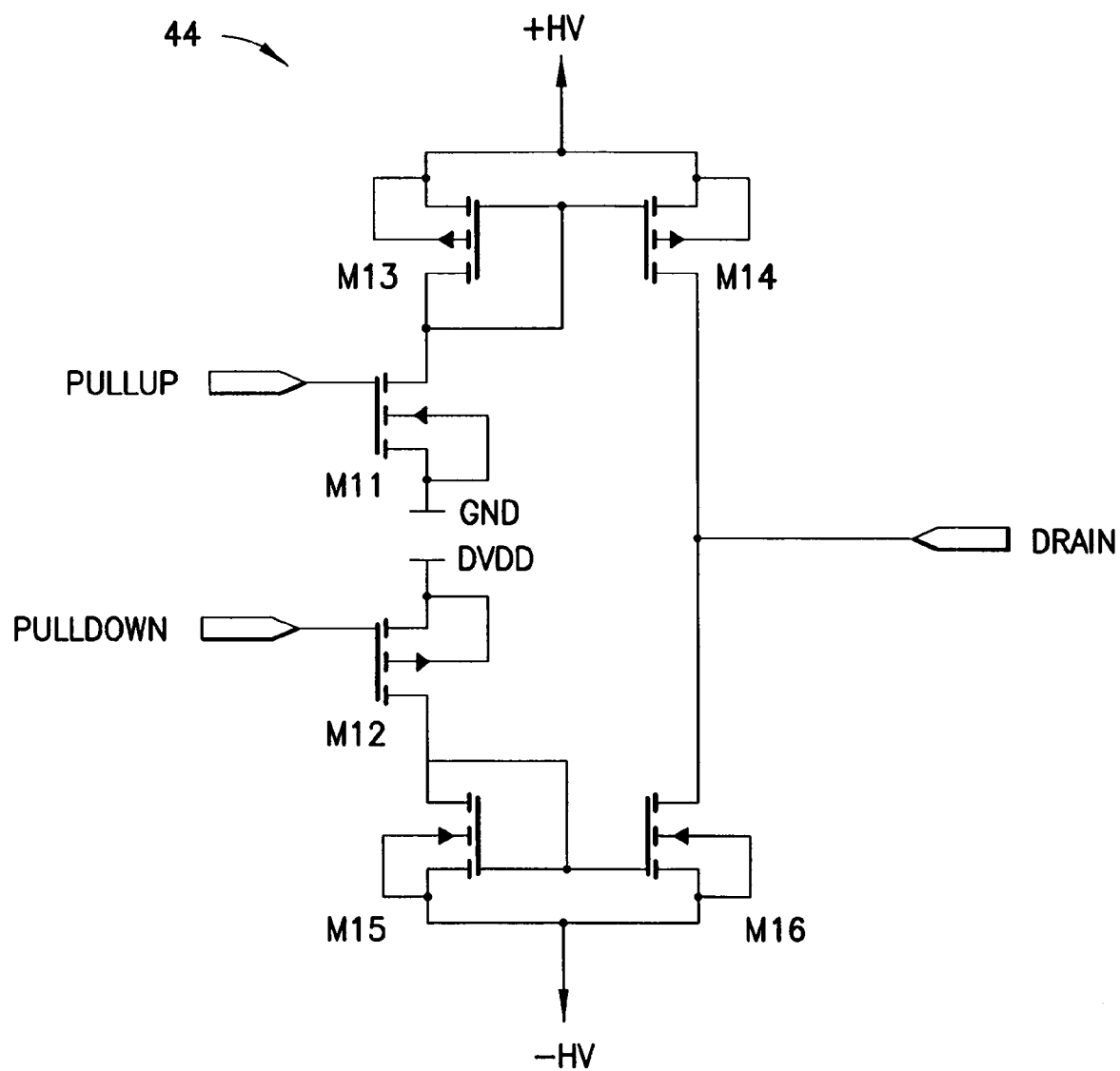
FIG. 8 is a circuit diagram showing a circuit implementation of the high-voltage pulser incorporated in the unit cell architecture shown in FIG. 5.

One implementation of the circuitry of the high-voltage pulser 44 is illustrated in FIG. 8. As previously noted, the pulser takes its inputs (PULLUP and PULLDOWN) from the splitter. There are two inputs: one to drive the pulser output high to +25 V and the other to drive it low to −25 V. Each pulser comprises FETs M11 to M16 connected as shown in FIG. 8.

Figure 9:
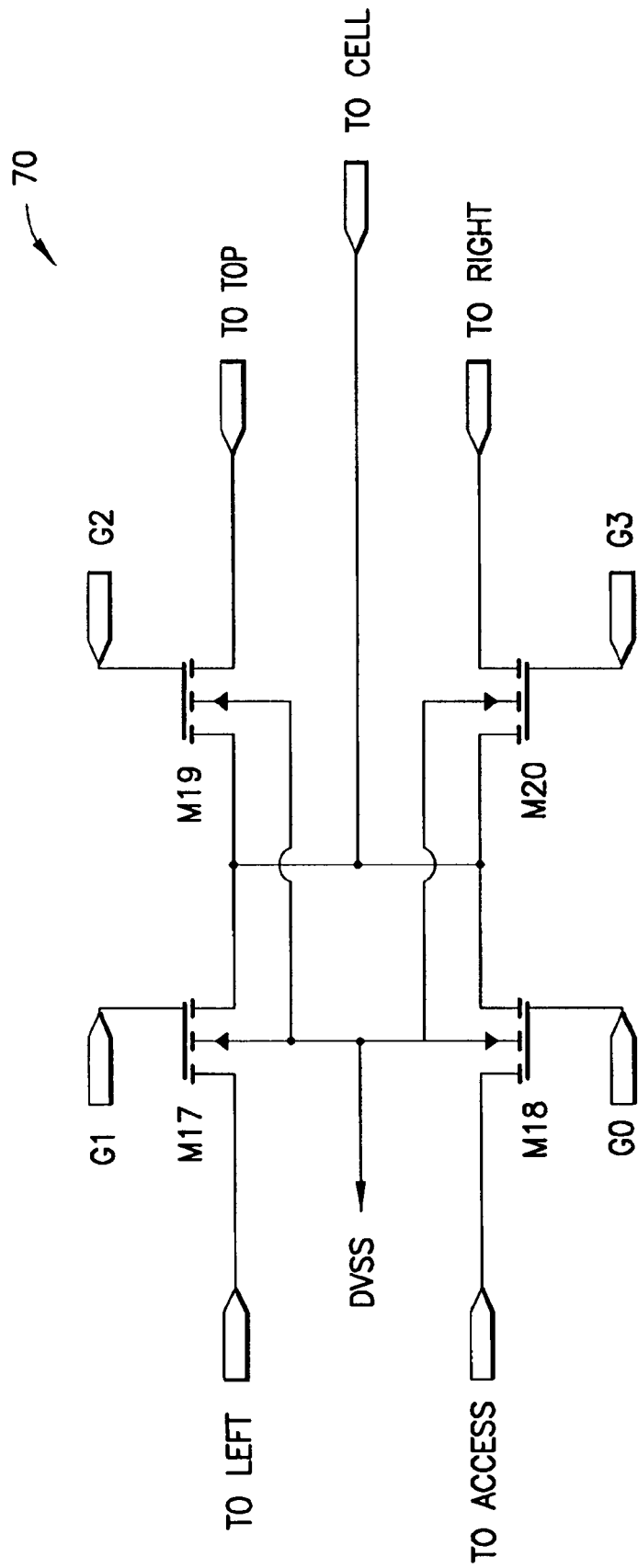
FIG. 9 is a circuit diagram showing a circuit implementation of the low-voltage switch network incorporated in the unit cell architecture shown in FIG. 5.

One implementation of the circuitry of the low-voltage switch network 70 is illustrated in FIG. 9 and comprises FETs M17 to M20. Transistor M18 serves as the access switch; transistors M17, M19 and M20 respectively serve as the matrix switches. All switches M17 to M20 meet at a common point 88 that is connected to the central node (node 78 in FIG. 5) in the unit cell. This node drives both the splitter input as well as the low-voltage side of the T/R switch through respective low-voltage transmission gates (71 and 72 in FIG. 5). The other terminals of the switches M17 to M20 are each connected as shown in FIG. 9, with two of the switches (M17 and M20) connected to horizontally adjacent cells (left and right) in the hexagonal matrix, one switch (M19) connected to the next above cell, and the last switch (M18) connected to the vertical signal access line (86 in FIG. 5). The CMOS cells are rectangular and designed to match with a hexagonal array of acoustical subelements, as described in U.S. patent application Ser. No. 10/751,290 entitled "Alignment Method for Fabrication of Integrated Ultrasound Transducer Array". Each of the four switches M17 to M20 is controlled by its own respective control signal G0 to G3. These are generated by the digital control circuitry (74 in FIG. 5), as described in detail below. These devices are floating low-voltage FETs. They must be placed in a low-voltage well biased at DVSS, which well in turn sits inside a low-voltage well biased at DVDD, which in turn sits inside the p substrate, which is biased at −HV.

Figure 10:
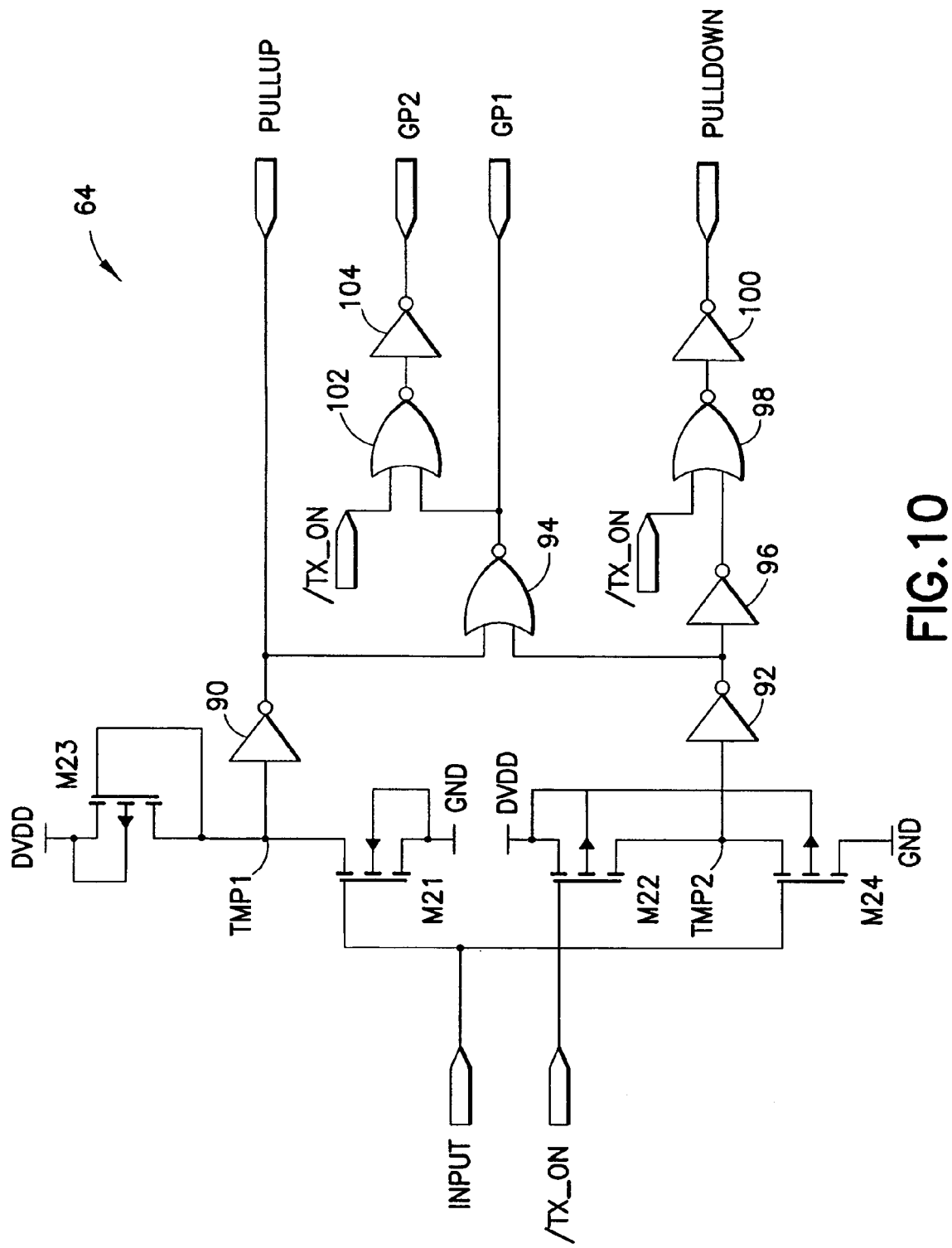
FIG. 10 is a circuit diagram showing a circuit implementation of the low-voltage splitter incorporated in the unit cell architecture shown in FIG. 5.

The circuitry of the splitter 64 is illustrated in FIG. 10. The splitter 64 consists of low-voltage floating transistors M21 to M24 followed by floating logic. The splitter circuit takes the input signal and creates control signals for driving the high-voltage T/R switch and the high-voltage pulser. The low-voltage floating transistors M21 to M24 must be placed in a low-voltage well biased at GND, which well in turn sits inside a low-voltage well biased at DVDD, which in turn sits inside the p substrate.

FIG. 10 shows a circuit implementation in CMOS technology of a bipolar-to-unipolar splitter. The input of the splitter is a bipolar pulse, whose signal levels are between +DVDD and −DVDD. The task of the splitter is not only to separate the timing information of the positive and negative cycles but also to convert the signal levels for each cycle into unipolar format, where the signal levels are between 0 and DVDD only.

One portion of the splitter circuitry (namely, FETs M21 and M23 and inverter 90) filters the bipolar input pulses and outputs only positive polar pulses. For the positive polar pulse at the input node INPUT in FIG. 10, M21 is turned on to pull down the node TMP1 to ground. Therefore, the following inverter 90 regenerates a solid logic level DVDD at the output node PULLUP. For the negative polar pulses at the input, the gate to source voltage for M21 is negative so that M21 is turned off, which results in the node voltage at TMP1 being +DVDD−$|V_{thr}|$, where $V_{thr}$ is the threshold voltage of M23. Since the node voltage at TMP1 is +DVDD−$|V_{thr}|$, the following inverter 90 regenerates a solid ground at the node PULLUP. There is no static power consumption when the input is 0 V.

Another portion of the splitter circuitry (namely, FETs M22 and M24 and inverters 92 and 96 in series) filters the bipolar input pulses and outputs only inverse positive polar pulses. For the positive polar pulse at the input node INPUT, M24 is turned off. M22 is always turned on, so that TMP2 is pulled up to +DVDD. Therefore, the following inverters 92, 96 and 100, in conjunction with 2NOR gate 98, regenerate a solid +DVDD at the output node PULLDOWN. For the negative polar pulses at the input node INPUT, the source to gate voltage for M24 is positive so that M24 is turned on, which pulls node TMP2 down and close to ground. Therefore, the following inverters 92, 96 and 100, in conjunction with 2NOR gate 98, regenerate a solid ground at the output node PULLDOWN. There is a static power consumption of M22 and M24 when the input is 0 V, and this static power consumption can be avoided by programming the gate voltage of M22.

FIG. 10 also shows the logic operations to generate the signals GP1 and GP2, which control the high-voltage T/R switch (66 in FIG. 5). The outputs of the inverters 90 and 92 are provided as inputs to a 2NOR gate 94. The output of 2NOR gate 94 is GP1. The signals GP1 and TX_ON are input to another 2NOR gate 102, which is followed by an inverter 104, the output of which is GP2.

Figure 11:
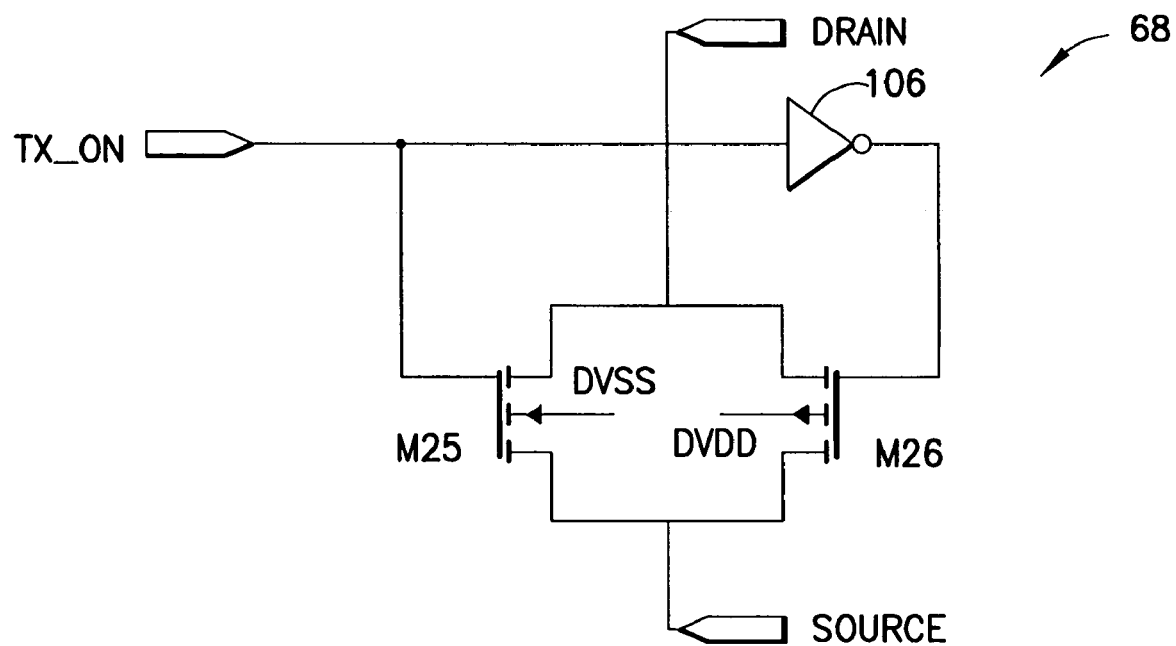
FIG. 11 is a circuit diagram showing one circuit implementation of the low-voltage ground switch incorporated in the unit cell architecture shown in FIG. 5. The low-voltage transmit switch and low-voltage receive switch can also be implemented in this way.

One implementation of the circuitry of the ground switch 68 is illustrated in FIG. 11. The ground switch comprises floating low-voltage FETs M25 and M26, and an inverter 106 that outputs RX_ON, an inverted TX_ON signal, to the gate of FET M26. FET M25 is placed in a low-voltage well biased at DVSS, which well in turn sits inside a low-voltage well biased at DVDD where FET M26 sits, which in turn sits inside the p substrate. The low-voltage transmit and receive switches (71 and 72 in FIG. 5) may also be implemented using the circuitry shown in FIG. 11.

Figure 12:
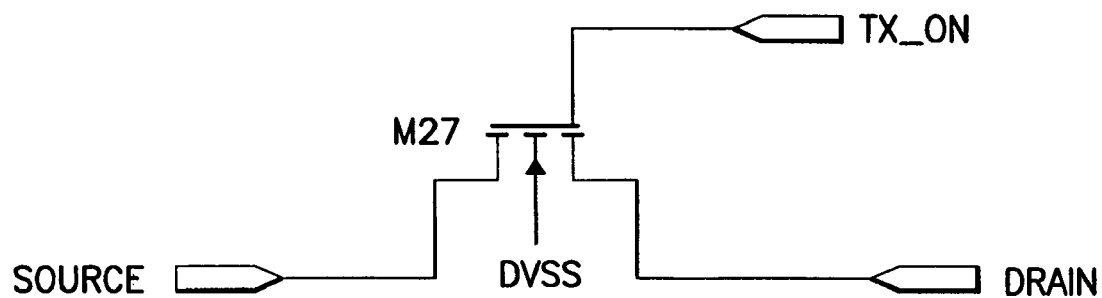
FIG. 12 is a circuit diagram showing an alternative circuit implementation of the low-voltage ground switch incorporated in the unit cell architecture shown in FIG. 5. Again, the low-voltage transmit switch and low-voltage receive switch can also be implemented in this way.

Alternatively, each of the low-voltage ground (68), transmit (71) and receive (72) switches may be implemented using the floating low-voltage FET M27 depicted in FIG. 12. FET M27 is placed in a low-voltage well biased at DVSS, which well in turn sits inside a low-voltage well biased at DVDD, which in turn sits inside the p substrate.

The circuitry shown in FIG. 11 will operate with inputs that are fully between DVSS and DVDD. The circuitry shown in FIG. 12 however will only operate between DVSS and DVDD–$V_{thr}$, where $V_{thr}$ is the threshold of the NMOS device (typically about 0.8 V). The advantage of using the circuit shown in FIG. 12 is that it is about 3 times smaller than the one shown in FIG. 11. The disadvantage is that, because the signal level it can pass is lower, it limits the dynamic range of the signals passing through it.

Another important difference between the low-voltage receive switch 72 and the low-voltage transmit switch 71 is that the latter can be a lot smaller than former since it can have a higher on resistance. This is due to the fact that the low-voltage transmit switch 71 is passing a signal to the gate of a small transistor (at the input of the splitter 64) which has low capacitance, whereas the low-voltage receive switch 72 is passing a signal to the access lines, which have a much higher capacitance.

As seen in FIG. 6, prior to transmit, the digital control circuitry (74 in FIG. 5) sends program data in the form of signals that control the state of the access switch and matrix switches of the associated low-voltage switching network 70, forming the transmit aperture by connecting subelements. Control of which pulsers are fired is set entirely by the dense low-voltage switching matrix. Configuration of the switches also dictates how signals are routed on receive.

Figure 13:
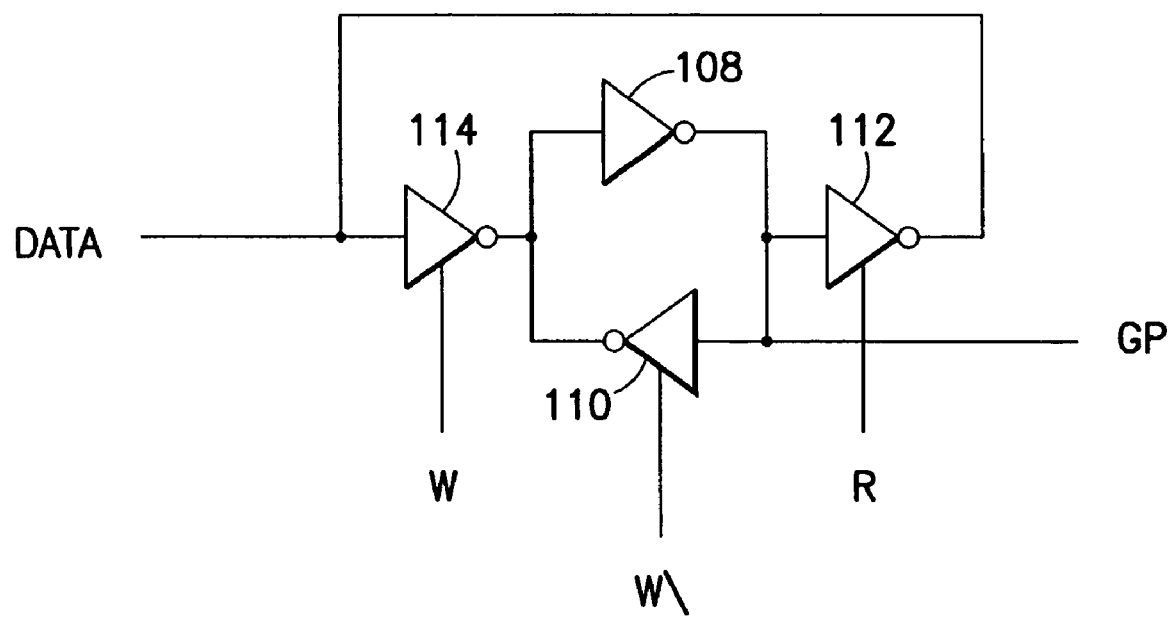
FIG. 13 is a circuit diagram showing one implementation of digital circuitry for a digital latch, four of which are included in the digital control block shown in FIG. 5.
Figure 14:
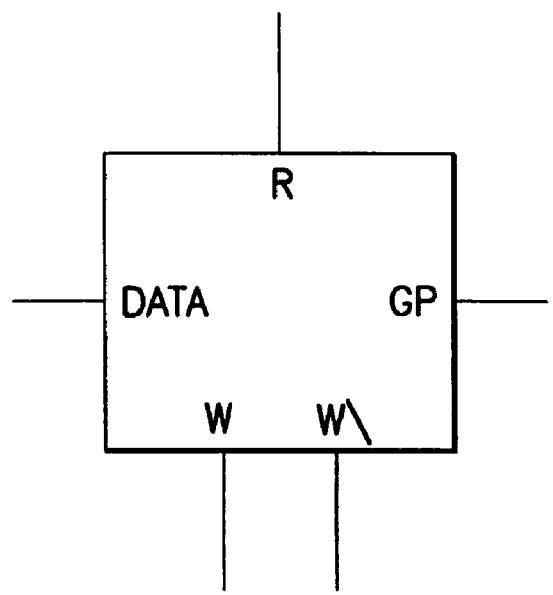
FIG. 14 is a drawing showing the hierarchical symbol for the unit switch cell digital latch depicted in FIG. 13.

Both of these switch states (transmit and receive) are stored locally in the digital control electronics (see discussion of FIGS. 13-15 below). Additionally these settings may be updated to be different from transmit to transmit as well as from individual transmit cycle to receive cycle. They may even be updated at multiple points during the receive cycle in order to allow for multiple focal zones during receive, as shown in FIG. 6.

In the current design, both the digital and analog signal lines are brought in on a single face of the array. In one implementation they are brought in on the top face of the array, extending in parallel with the columns of cells. As seen in FIG. 5, the cell matrix addressing architecture has distributed low-voltage access lines 86. Digital switch state data is programmed into the array on multiple four-bit data bus lines 82. Each row has a unique address and columns are programmed in parallel. Each cell in each column is connected to all four digital data lines.

Also in the current design, selection is done using a series of select lines. Each row has one digital address select line 84 that selects all cells on that row in parallel simultaneously. Once the cells are selected, they all latch the data on their respective column bus lines 82 simultaneously. Since only one face of the array can be used for pad access, these digital select lines 84 must be brought in along the columns and then converted to run across the rows. This is done using junctions that tie the row address select lines to the column address select lines. There are two address lines in each column and two junctions to respective row lines in each column. The use of address select lines integrated in each row of the array simplifies the digital circuitry in each cell since there is no need for an address decoder and no need for a latch to store the addressed state. The above-described select line and other addressing methods are disclosed in U.S. patent application Ser. No. 10/978,012 filed on Oct. 29, 2004 and entitled "Method and Apparatus for Controlling Scanning of Mosaic Sensor Array. The other addressing methods disclosed in that filing could also be used with the present invention.

Still referring to FIG. 5, the digital control circuitry 74 outputs control signals G0-G3 that control the state of the access and matrix switches in the low-voltage switch network 70. Only one control signal is required for each analog switch because the switches are low voltage and are operated simply using logic levels. The digital control circuitry 74 operates around GND while the substrate is biased at –HV. Therefore the digital control circuitry is also placed in a low-voltage well biased at DVSS, which well in turn sits inside a low-voltage well biased at DVDD, which in turn sits inside the p substrate.

The digital control circuitry 74 in each cell comprises four latches (L0 to L3 shown in FIG. 15), which hold the current state of the access and matrix switches in the low-voltage switch network 70. The latches can be written to as well as read so that they can be tested. FIG. 13 shows the logic contained within each latch. These are static latches composed of two cross-coupled inverters 108 and 110 along with additional inverters 112 and 114 for read and write capability respectively. Programming of the latch is done by asserting the write line W, causing data to be stored on the input capacitance of the top inverter 108 in the cross-coupled pair. Data is read back on the DATA line by asserting the read line R, causing the tri-state output inverter 112 to drive the state of the DATA line to reflect the state of the latch. Read data is the inverse of write data. The output of the latch appears on the GP line and is fed to a respective switch control circuit (not shown), which controls the state of the corresponding switch in the low-voltage switch network 70. A hierarchical symbol for the unit switch cell digital latch can be seen in FIG. 14. While SRAM cells are described here, the invention could also make use of other memory technologies currently available (such as DRAM, MRAM, FRAM, EPROM, etc.) as well as any other future technologies to be developed.

Figure 15:
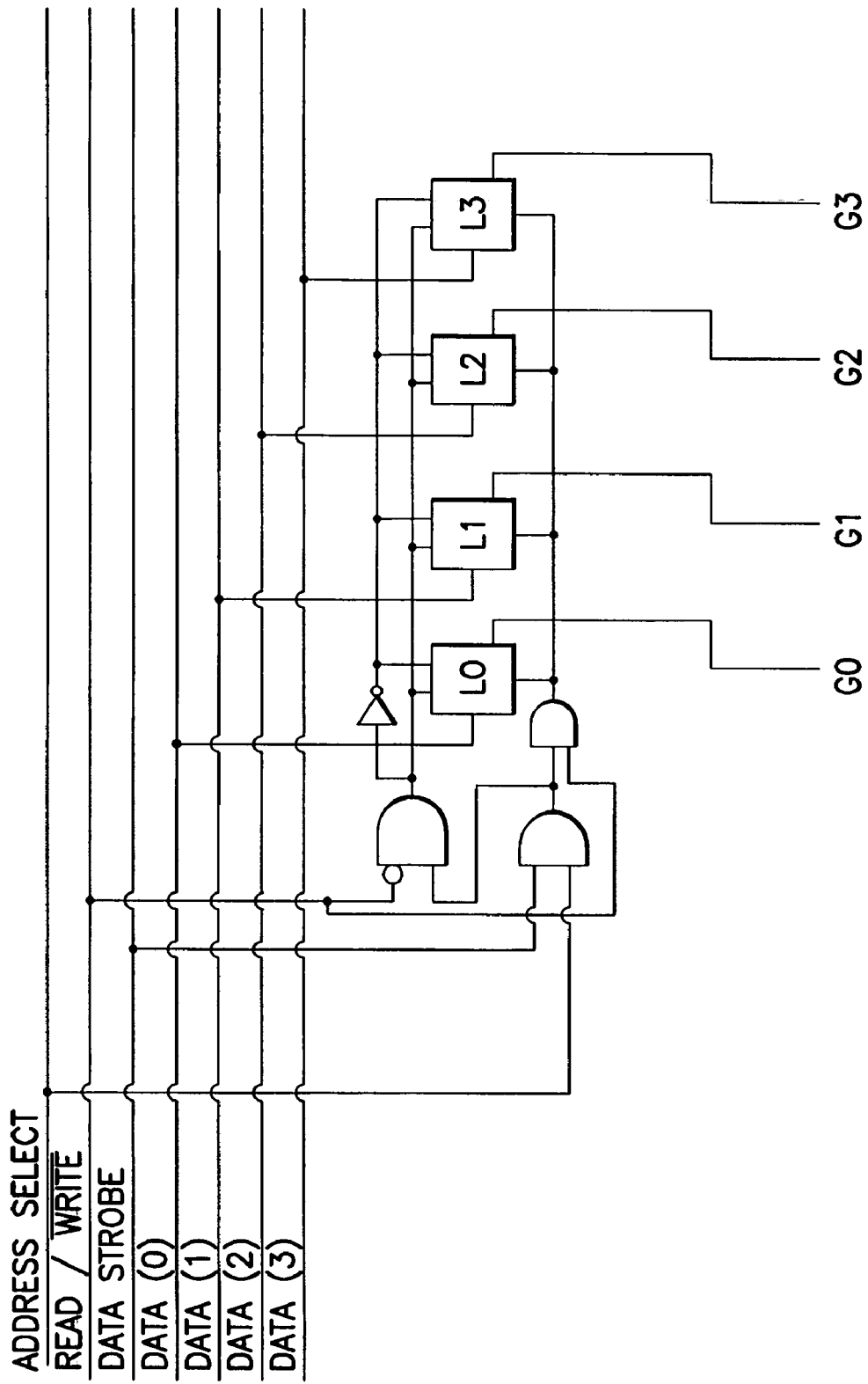
FIG. 15 is a circuit diagram showing one circuit implementation of the digital control block shown in FIG. 5.

In addition to the four latches, each switch cell also contains addressing and control logic as shown in FIG. 15. FIG. 15 also shows digital control lines and a 4-bit data bus. As shown, the bus runs down each column such that all of the other switch cells on this column (not shown) share the bus as well. Note that for simplicity the bus is shown horizontal while in reality it will be vertical. Unique addresses for each row are generated off chip and distributed on each column. These address lines are fed into the Address Select line as shown in FIG. 15. Each interface unit cell will have a number of traces running through it to supply power, analog signals and digital control signals.

Figure 16:
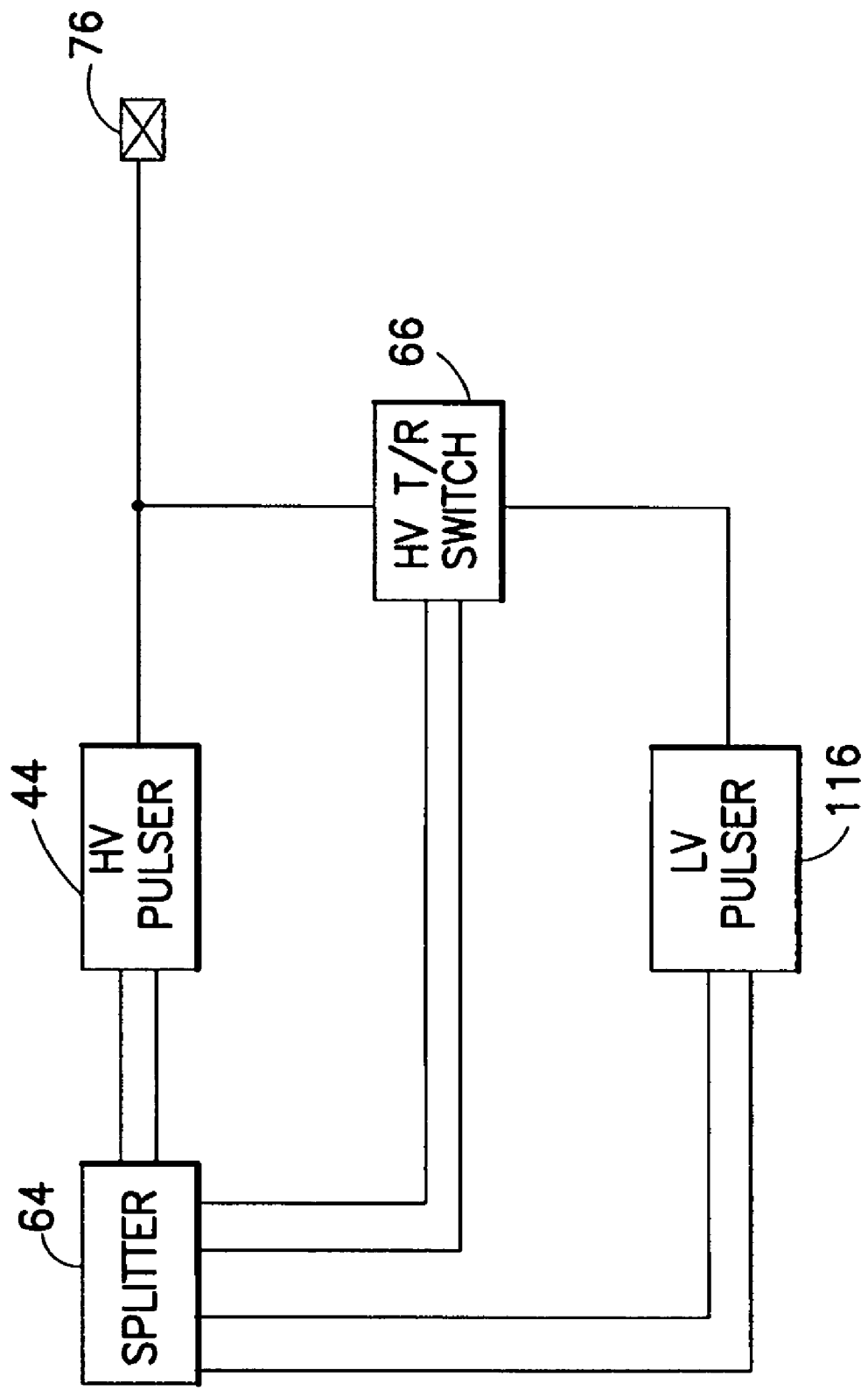
FIG. 16 is a block diagram showing an interface array unit cell architecture having both a high-voltage pulser and a low-voltage pulser in accordance with another embodiment of the present invention.

A further improvement of the invention for Doppler purposes involves the addition of a low-voltage pulser 116, as seen in FIG. 16. In this design, the low-voltage pulser 116, which is used for Doppler transmit, is protected from the high-voltage pulser 44 by the high-voltage T/R switch 66. A global signal (not shown in FIG. 16) received by the splitter 64 controls selection between Doppler and B-Mode operation. For Doppler operation, the splitter 64 selects the low-voltage pulser 116 and turns on the high-voltage T/R switch 66 so that the output of the low-voltage pulser 116 is routed to the transducer via pad 76. It also prevents the low-voltage pulser from driving the low-voltage switching matrix (not shown in FIG. 16) by turning off the low-voltage receive switch (not shown in FIG. 16). For B-Mode operation, the splitter 64 selects the high-voltage pulser 44 and turns off the high-voltage T/R switch 66. In this way it is possible to acquire both Doppler and B-Mode information using a highly integrated interface array.

A further improvement of the invention is the use of multiple pulser voltage supply lines for both the positive and negative pulse voltages. These lines may be distributed individually on each column in the array, on each row or along diagonals. Since each voltage line is individually assigned a voltage, it becomes possible to have different columns and rows of interface cells transmit using different voltage levels. Typically the variation approximates some curve or window where the highest transmit voltage occurs at the center of the aperture and low voltages occur on either side of the center. This capability is especially important when using apodization to reduce grating lobes by smoothing out the effects of truncated apertures.

Figure 17:
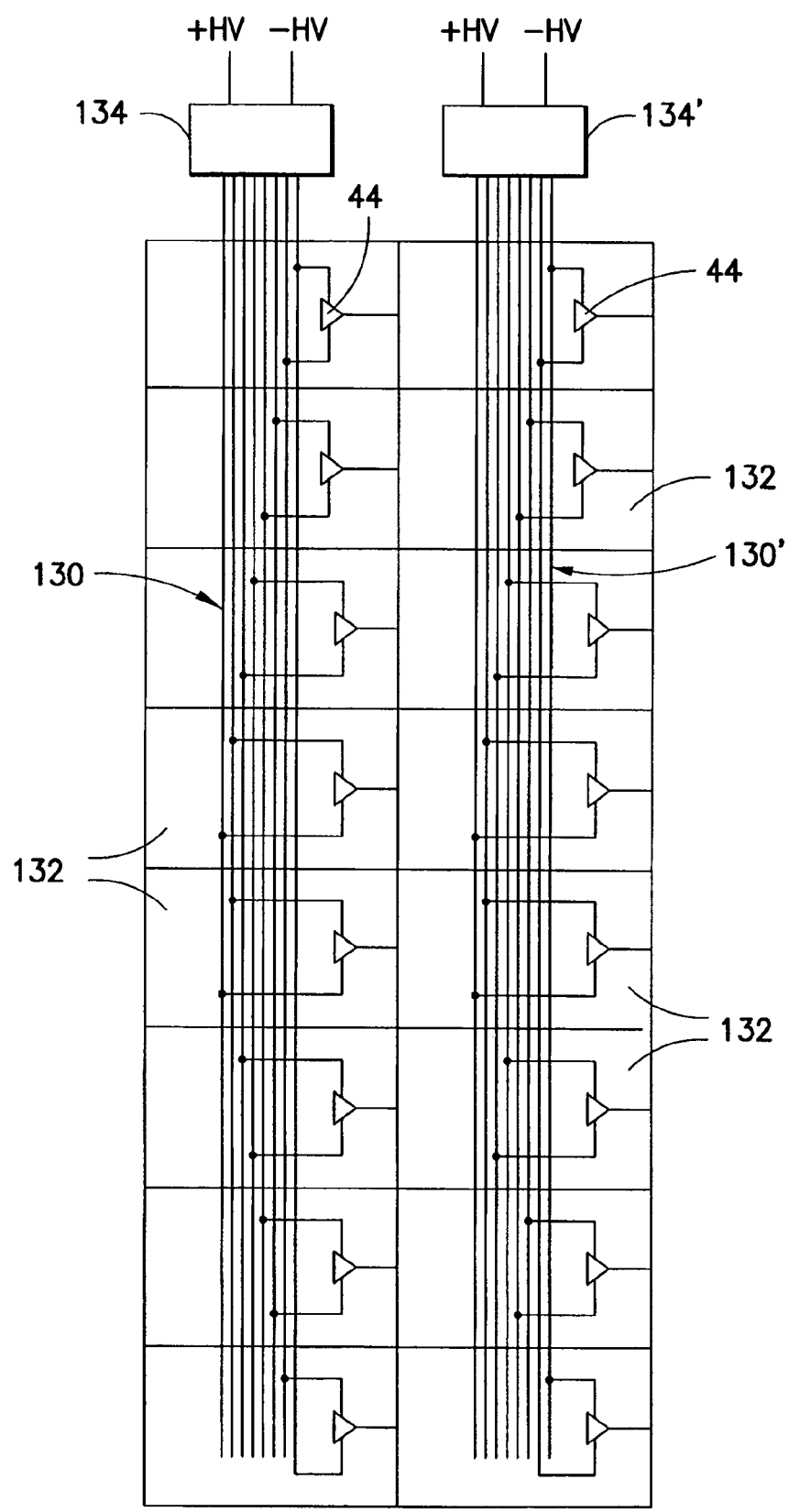
FIG. 17 is a drawing showing an arrangement of power supply lines that enables the pursers to be operated at different voltages.

FIG. 17 shows an arrangement of power supply lines that enables the pulsers 44 in different columns of interface circuit cells 132 to be operated at different voltages. In this example, power is applied to the power supply lines 130 in the left-hand column of cells by a multichannel variable output level voltage supply 134, while power is applied to the power supply lines 130' in the right-hand column of cells by another multichannel variable output level voltage supply 134'. Thus, the left- and right-hand columns of acoustical subelements (corresponding to respective interface circuit cells) can transmit using different voltage levels.

The interface cell array disclosed herein is ideally placed directly in the substrate upon which the cMUT cells are constructed, but can also be in a different substrate integrated adjacent to the transducer substrate. Since cMUT arrays are built directly on top of a silicon substrate, the interface electronics can be incorporated into that substrate. For a PZT or more conventional implementation, the interface electronics would simply be fabricated in a separate silicon substrate and attached to the PZT array.

Figure 18:
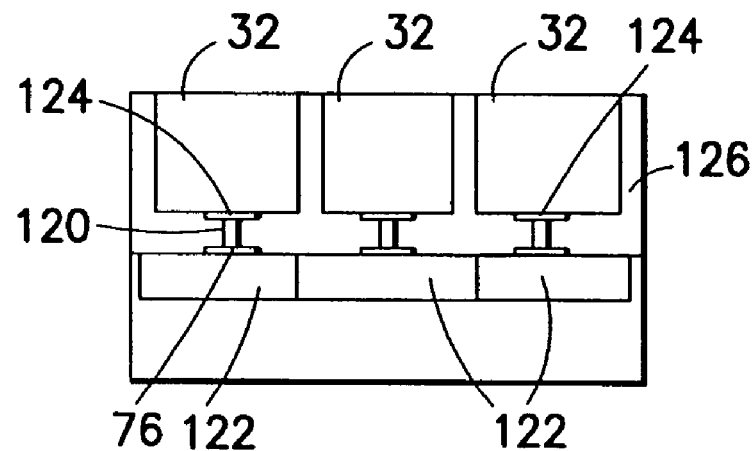
FIG. 18 is a drawing showing a cross-sectional view of a co-integrated cMUT and application specific integrated circuit (ASIC) interface cell array incorporating the circuitry depicted in FIG. 5.

A cross-sectional view of a co-integrated cMUT and ASIC array is shown in FIG. 18 to illustrate how the connections would be made from the ASIC to the cMUTs. As shown, a single via 120 is used to connect each cMUT subelement 32 to its counterpart CMOS interface cell 122. The vias 120, which connect the pads 124 of the signal electrodes to respective conductive pads 76 formed on the interface ASIC, may be embedded in an acoustic backing layer 126 or other suitable insulating material.

Figure 19:
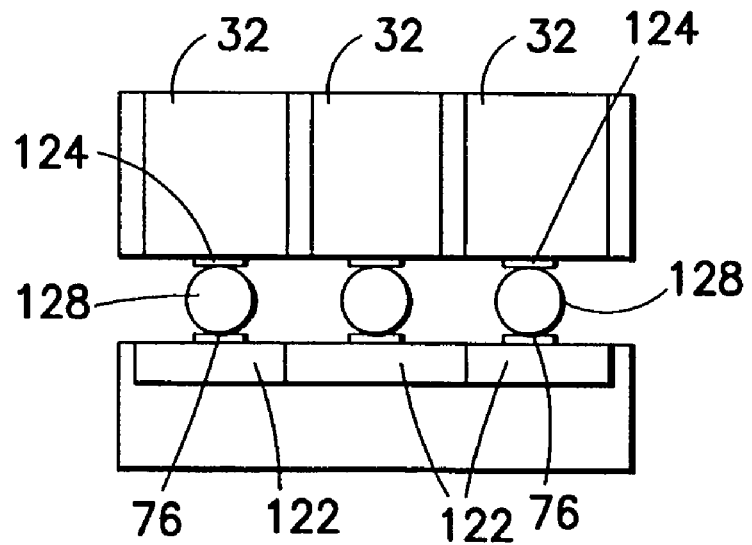
FIG. 19 is a drawing showing a cross-sectional view of a cMUT device substrate connected to an ASIC interface cell array incorporating the circuitry depicted in FIG. 5.

It is also possible to build the cMUTs on a separate substrate (e.g., a wafer) and connect them to the ASIC interface cell matrix separately, as shown in FIG. 19. Here for example, electrically conductive bumps 128 and electrically conductive pads 76 and 124 are used to connect the individual cMUT subelements 32 to their counterpart interface cells 122. Other interconnect techniques such as anisotropic conductive paste (ACP), anisotropic conductive film (ACF), electrically conductive polymers, metallized bumps, vertical interconnect systems, e.g., z-axis interposers, flexible printed circuits, etc. or metallized vias could also be used.

In accordance with the constructions shown in FIGS. 18 and 19, the pulsers and low-voltage switching network would be disposed in the probe head rather than in the probe handle, as depicted in FIG. 4.

One aspect of the invention provides a large array of small and identical interface cell circuits, each comprising a transmitter, a T/R switch, associated control and decoding circuitry as well as a switching matrix for routing the control signals. The interface cell circuit has bipolar operation due to the use of a return-to-zero circuit (i.e., the ground switch). The interface cell circuit incorporates a splitter circuit to decode the analog input control signal. In accordance with one variation, the interface cell circuit is made Doppler-capable by adding a low-voltage pulser behind the T/R switch. Multiple separate pulser voltages on each column allow for apodization.

The invention provides low-power and high-density interface electronics for a dense ultrasound array. Since the control signals for the pulsers are low-voltage signals, they can easily be routed using a low-voltage switching matrix. This yields a tremendous savings in terms of area since high-voltage switches are generally 3 to 4 times larger than equivalent-resistance low-voltage devices. In addition, the larger high-voltage switches also have much higher associated parasitic capacitances due to their size. Therefore, there is also a power savings associated with not having to drive a large parasitic capacitance when transmitting into the switching matrix. This fact, coupled with the vast reduction in parasitics due to the transducer cable, means that the pulsers themselves can be made much smaller since they do not have to drive as much peak current. These features make it possible to integrate the pulsers within each interface cell since they are now orders of magnitude smaller than what was possible with the pulsers outside of the matrix. The low parasitics also reduce signal attenuation due to loading of the cMUTs on receive.

The invention provides the following advantages over existing systems and prior art: 1) reduced power consumption since pulsers are integrated directly next to the transducers and no parasitic capacitances need to be driven. 2) reduced power in the control circuitry due to the use of dynamic control signals 3) highly integrated architecture which greatly reduces the size of board electronics 4) potentially increased image resolution due to the small size of the individual pulsers.

Figure 20:
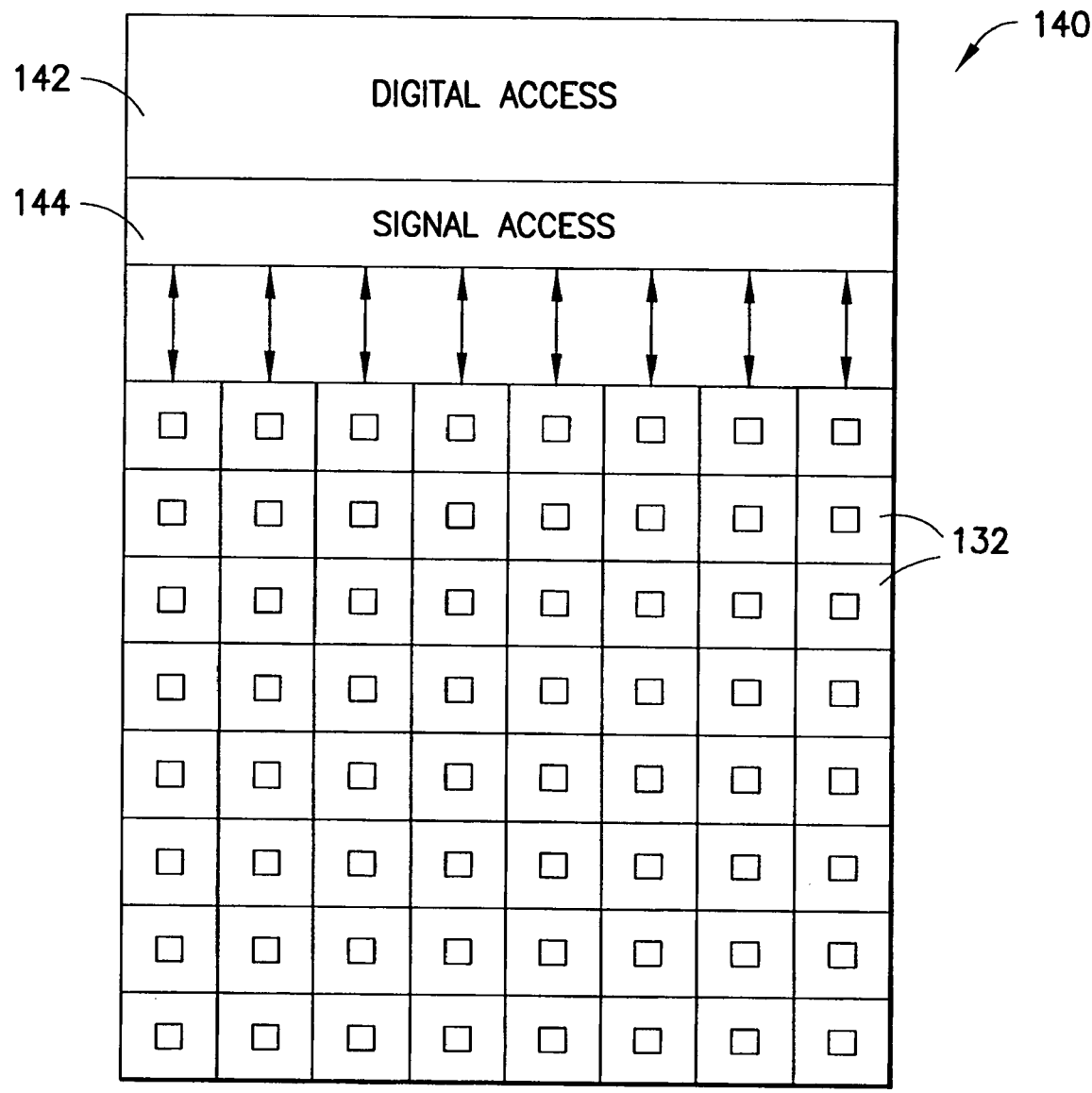
FIG. 20 is a drawing showing the layout for the digital and analog signal lines for chips that can be tiled together to form an array.
Figure 23:
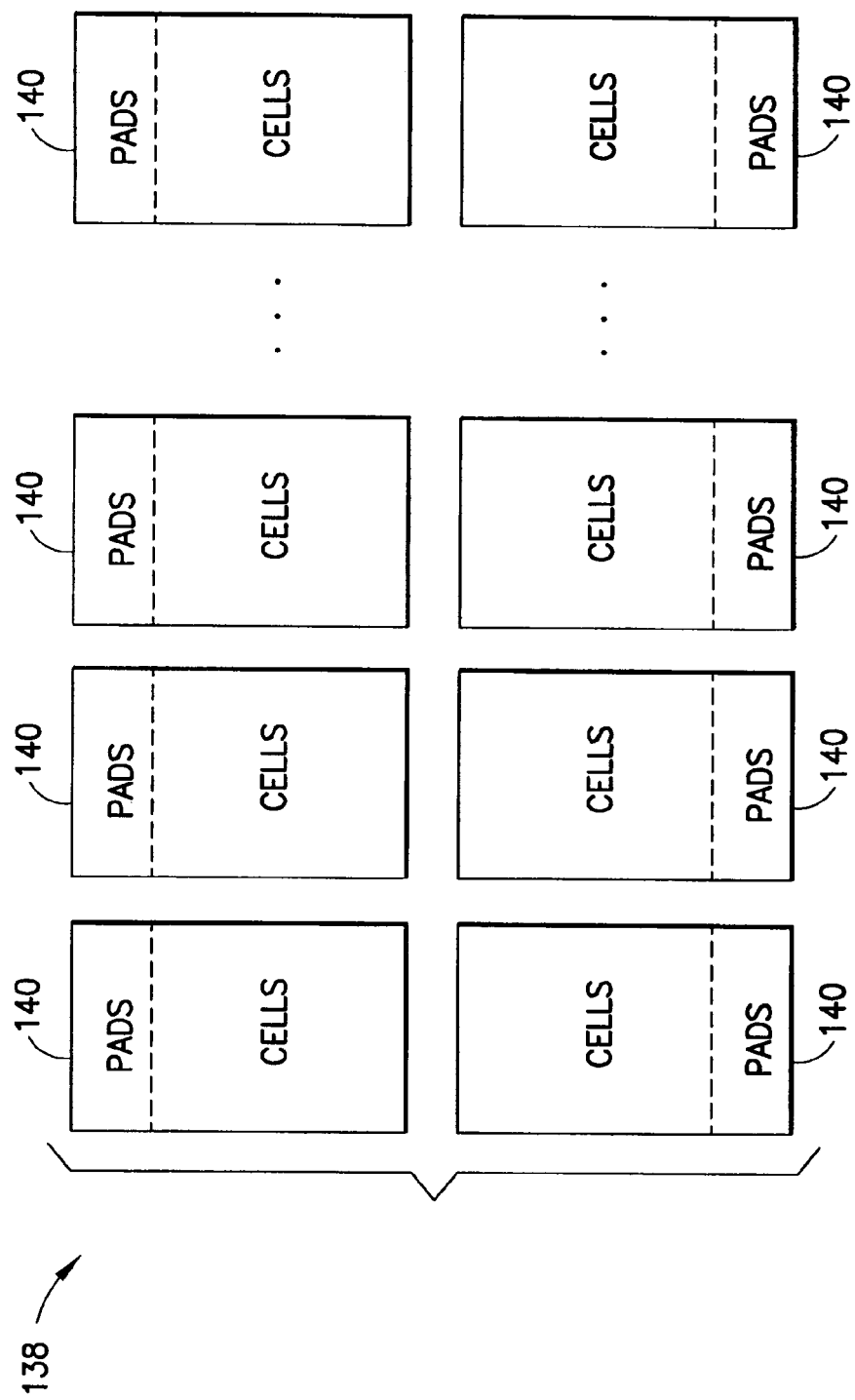
FIG. 23 is a drawing showing a plurality of chips of the type shown in FIG. 20 tiled together to form a single transducer array.

In accordance with a further embodiment of the invention, addressing into the array is done in two parts as shown in FIG. 20. The digital and analog signal lines are both brought in on a single face of a chip 140. Then a plurality of such chips 140 are tiled together to build up a single transducer array 138, as seen in FIG. 23. In accordance with one design, each chip consists of a 32×64 cell array comprising transducers built on top of an array of interface circuit cells of a type previously described. Using a single face in this way allows the build up of larger arrays by tiling together multiple copies of the 32×64 cell array.

Figure 21:
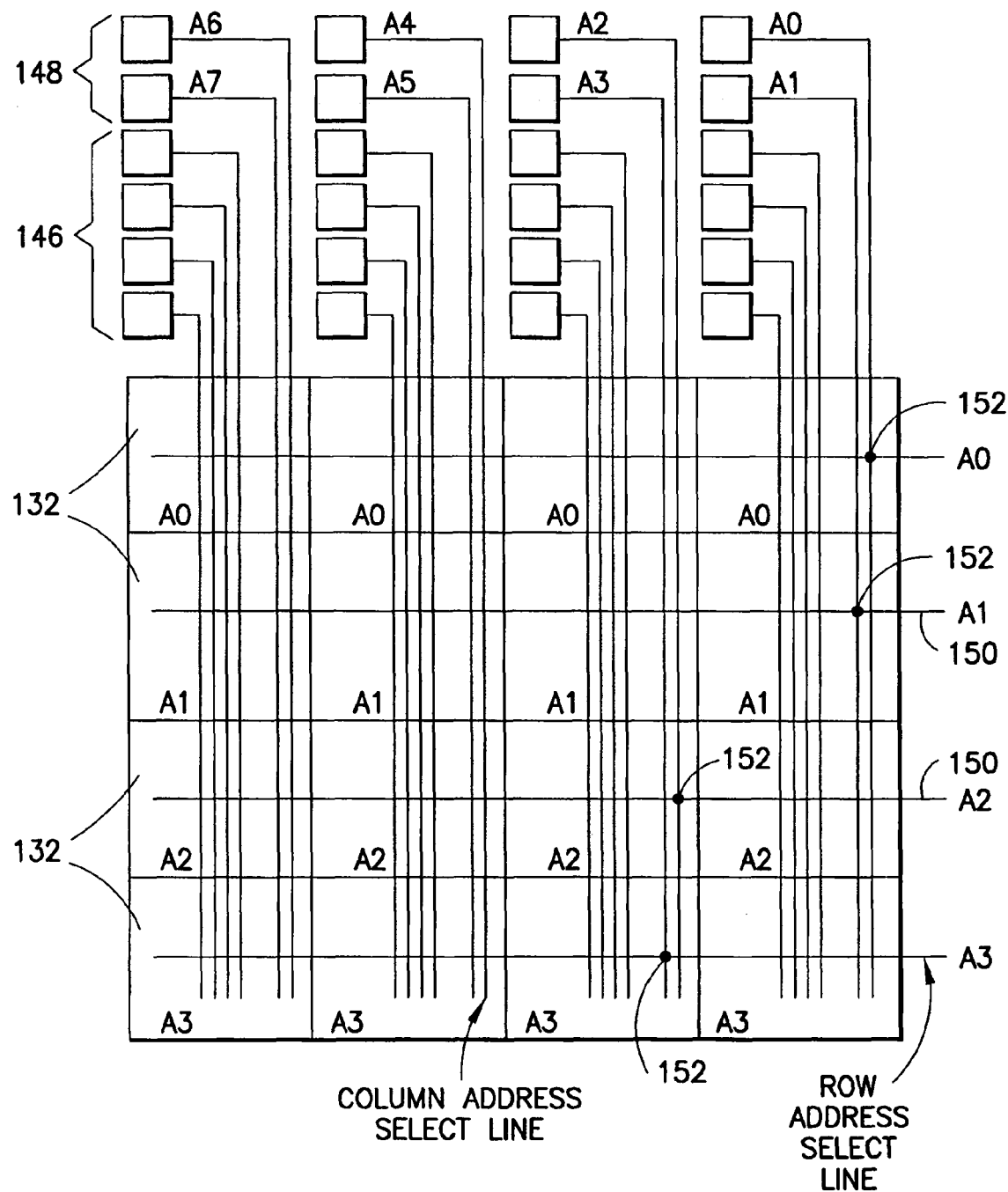
FIG. 21 is a drawing showing how the digital access lines are distributed (only 4 columns out of 16 are shown) on a chip of the type shown in FIG. 20.
Figure 22:
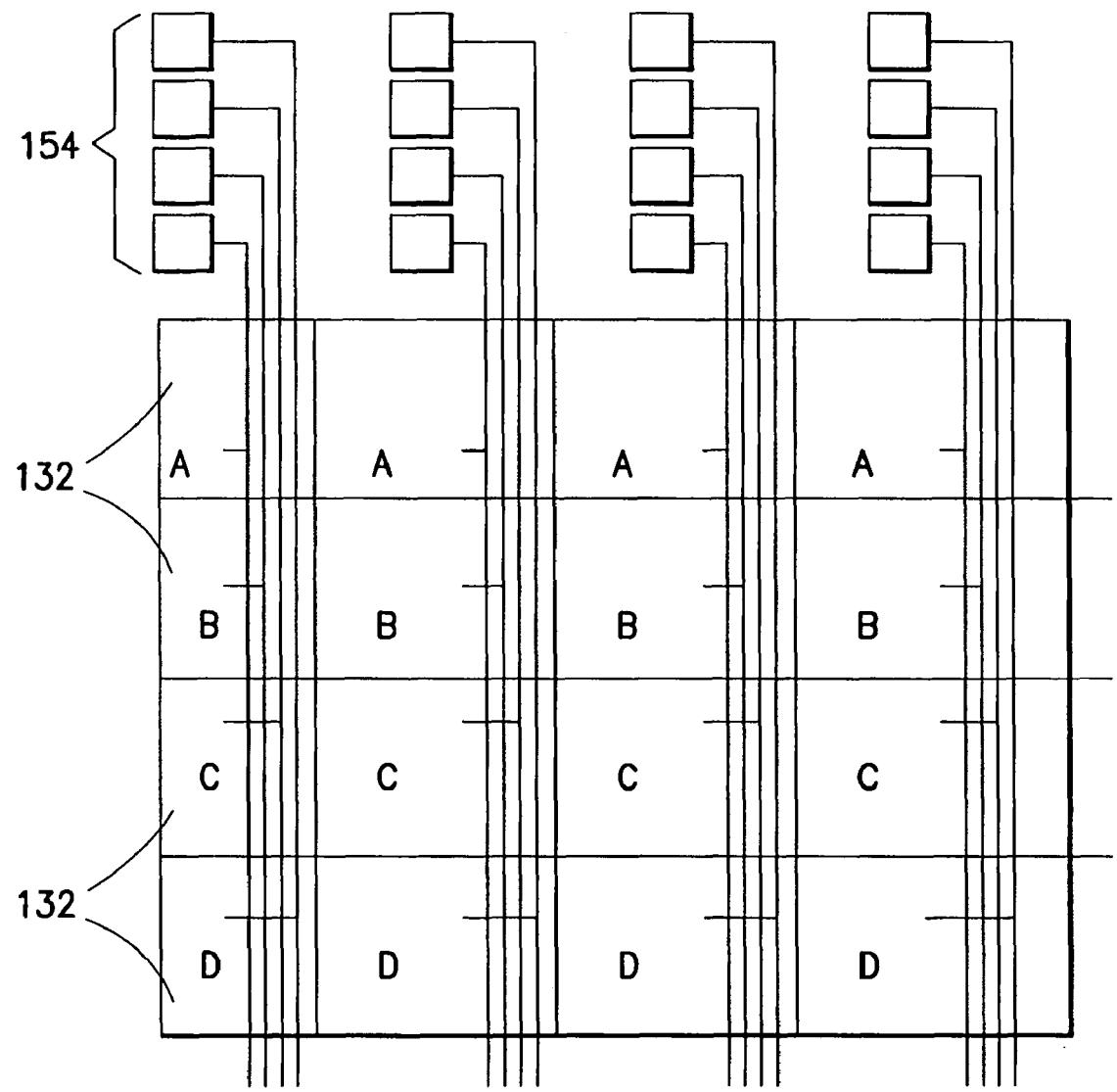
FIG. 22 is a drawing showing how the analog signal lines are distributed (only 4 columns out of 16 are shown) on the chip shown in FIG. 20.

A more detailed view of the addressing is illustrated in FIGS. 21 and 22. FIG. 21 shows how the digital access lines are distributed (only 4 columns out of 16 are shown). Digital data is programmed into the array on multiple four-bit data bus lines. Each row has a unique address (A0, A1, etc.) and that columns are programmed in parallel. Each cell 132 in each column is connected to all four digital data lines as shown.

Selection is done using a series of select lines as shown in FIG. 21. Each row has one digital select line 150 that selects all cells in that row in parallel simultaneously. The digital data line pads 146 and the address line pads 148 are disposed along one face of the array. Since only one face of the array is used for pad access, the digital select lines 150 must be brought in along the columns and then converted to run across the rows. This is done using junctions 152 that tie the row address select lines to the column address select lines, as shown in FIG. 21. There are two address lines in each column and two junctions to respective row lines in each column.

FIG. 22 shows how the analog signal lines are distributed. Access to each column of the array is from the top only as shown. Within a given column, every first cell is connected to the "A" signal line which is connected to a pad 154 at the top of the array, while every second cell is connected to the "B" signal line, every third cell to the "C" signal line and every fourth cell to the "D" signal line. This design requires four analog signal lines in each column. The pads 154 for all of these lines are located along the top face of the array as shown.

Figure 24:
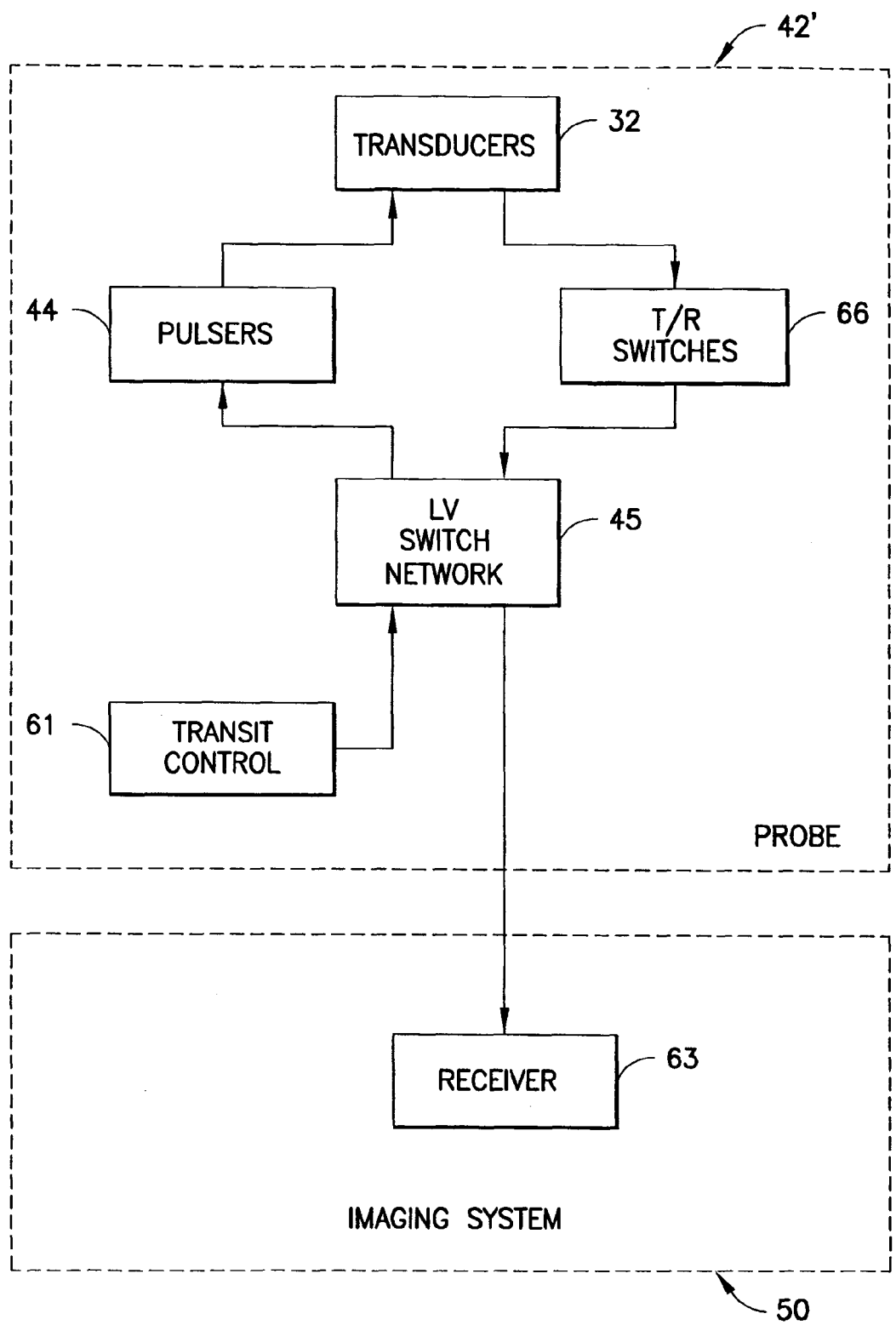
FIG. 24 is a block diagram representing portions of a transducer probe connected to an imaging system via cables in accordance with another embodiment of the present invention, wherein the transmit control circuits are also located on the probe.

In accordance with a further embodiment of the invention shown in FIG. 24, the transmit control circuitry 61 (including pulse timing circuitry) may be incorporated in the handle of a probe 42', while the transducers 32, pulsers 44, T/R switches 66, and low-voltage switching network 45 are incorporated in the head of the probe. The analog receive signals are sent to a receiver 63 of the imaging system 50 via a cable (not shown in FIG. 24).

Figure 25:
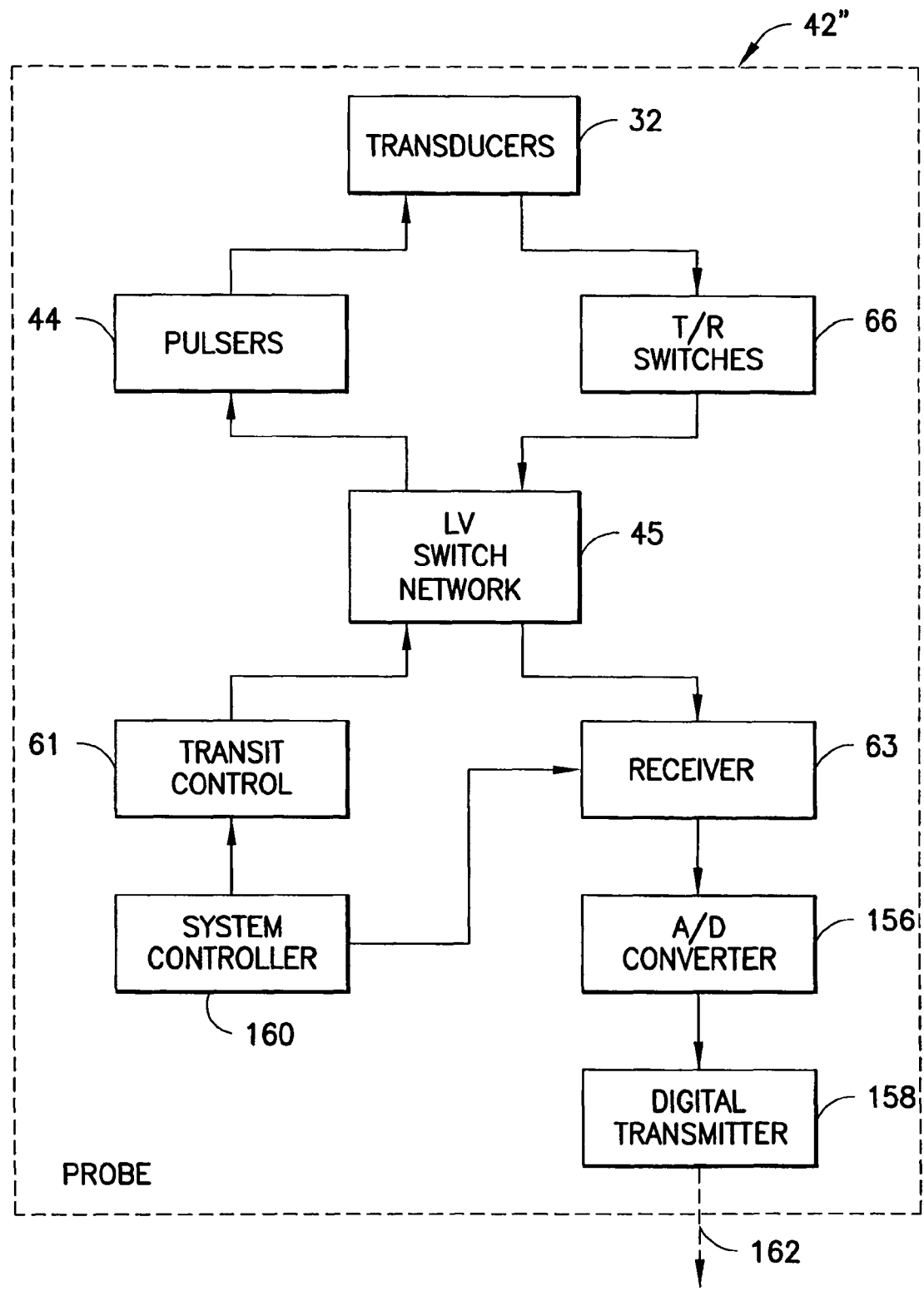
FIG. 25 is a block diagram representing portions of a transducer probe connected to an imaging system via cables in accordance with one embodiment of the present invention, wherein the transmit control circuits and the receiver are also located on the probe.

In accordance with yet another embodiment of the invention shown in FIG. 25, the receiver 63 is incorporated into the handle of a probe 42", along with the transmit control circuitry 61, while the transducers 32, pulsers 44, T/R switches 66 and low-voltage switching network 45 are incorporated in the head of the probe. The transmit control circuitry 61 and receiver 63 are controlled by a system controller 160, also incorporated in the probe 42". The receive beamformed analog data is output by the receiver 63 to an analog-to-digital converter 156, which in turn outputs the digital receive beamformed data to a data transmitter 158 that sends the data to a digital receiver of an imaging system (not shown in FIG. 25). The digital data link between the digital transmitter 158 on the probe 42" and the digital receiver of the imaging system may be wireless, fiber-optic or other wired high-data-rate link.

While the invention has been described with reference to particular embodiments, it will be understood by those skilled in the art that various changes may be made and equivalents may be substituted for elements thereof without departing from the scope of the invention. For example, although the disclosed embodiments use cMUTs, other ultrasonic transducer technologies could be used, including PZT, pMUTs and PVDF and any future transducer technologies could also be used. In addition, many modifications may be made to adapt a particular situation to the teachings of the invention without departing from the essential scope thereof. Therefore it is intended that the invention not be limited to the particular embodiments disclosed as the best mode contemplated for carrying out this invention, but that the invention will include all embodiments falling within the scope of the appended claims.

The invention claimed is:

1. A device comprising a multiplicity of ultrasonic transducers and a multiplicity of interface circuit cells, each of said ultrasonic transducers being electrically coupled to a respective one of said interface circuit cells, and each of said interface circuit cells comprising a high-voltage pulser for driving a respective ultrasonic transducer, a low-voltage switch for providing pulser control signals when said low-voltage switch is on, a low-voltage digital control circuit that outputs switch state control signals for controlling the state of said low-voltage switch, and a high-voltage transmit/receive switch disposed between said low-voltage switch and the respective ultrasonic transducer for providing a path for receive signals from the respective ultrasonic transducer to said low-voltage switch when said transmit/receive switch is on, wherein said transmit/receive switch blocks the pulser output from reaching said low-voltage switch via said path when said transmit/receive switch is off, and a low voltage splitter having a first input coupled to receive pulser control signals passed through said low-voltage switch, and an output in electrical connection with said high-voltage pulser.

2. The device as recited in claim 1, wherein said splitter is configured to separate said pulser control signals into a positive cycle pulser control signal and a negative cycle pulser control signal that are sent from first and second outputs respectively, said pulser comprising respective inputs for receiving said positive and negative cycle pulser control signals.

3. The device as recited in claim 2, wherein said splitter has a second input coupled to receive a transmit mode signal, and third and fourth outputs for outputting transmit/receive switch control signals to said transmit/receive switch for controlling the state of said transmit/receive switch, said transmit/receive switch control signals being a function of said pulser control signals and said transmit mode signal.

4. The device as recited in claim 1, wherein each of said interface circuit cells further comprises a low-voltage ground switch disposed between ground and said transmit/receive switch for allowing said path to float when said ground switch is off and said transmit/receive switch is on, said low-voltage ground switch providing a low-impedance path to ground during the transmit cycle so that the transducer can be discharged to ground whenever the transmit/receive switch turns on.

5. The device as recited in claim 1, wherein each of said ultrasonic transducers comprises a respective multiplicity of micromachined ultrasonic transducer cells that are electrically interconnected and not switchably disconnectable from each other.

6. The device as recited in claim 1, wherein each of said interface circuit cells further comprises a respective low-voltage pulser that is protected from a respective one of said high-voltage pulsers by a respective one of said high-voltage transmit/receive switches.

7. The device as recited in claim 1, wherein said ultrasonic transducers and said interface circuit cells are supported by a substrate having four sides, further comprising first and second sets of pads disposed within a marginal area extending along one of said four sides whose footprint does not overlap the footprint of the area in which said interface circuit cells are disposed, a first set of electrical conductors for connecting said first set of pads to respective ones of said low-voltage digital control circuits, and a second set of electrical conductors for connecting said second set of pads to respective ones of said low-voltage switches.

8. The device as recited in claim 1, further comprising means for providing multiple voltage levels to said pulsers.

9. The device as recited in claim 1, further comprising means for updating the receive aperture multiple times during a receive cycle.

10. A probe comprising: a multiplicity of ultrasonic transducers; a multiplicity of high-voltage pulsers coupled for respectively driving said transducers in accordance with low-voltage pulser control signals inputted to said probe in a transmit mode; and a multiplicity of high-voltage transmit/receive switches, each of said high-voltage transmit/receive switches having an input electrically connected to a junction at an electrical connection between a respective high-voltage pulser and a respective ultrasonic transducer and having an output, any signal at said input being passed to said output in a receive mode and being not passed to said output in said transmit mode, a multiplicity of low-voltage switches, each of said high-voltage pulsers configured to receive respective low-voltage pulser control signals derived from signals that pass through a respective one of said low-voltage switches, and a multiplicity of low-voltage splitters, each of said low-voltage splitters having a first input coupled to receive respective low-voltage pulser control signals passed through a respective one of said low-voltage switches, and each of said low-voltage splitters having an output in electrical connection with a respective one of said high-voltage pulsers.

11. The probe as recited in claim 10, wherein each of said low-voltage switches is configured to receive acquired data signals that pass through a respective one of said high-voltage transmit/receive switches in said receive mode.

12. The probe as recited in claim 10, wherein each of said low-voltage splitters has circuitry for separating said respective low-voltage pulser control signals into a positive cycle pulser control signal and a negative cycle pulser control signal that are sent from first and second outputs respectively, each of said high-voltage pulsers having first and second inputs for respectively receiving said positive and negative cycle pulser control signals.

13. The probe as recited in claim 12, wherein each of said low-voltage splitters has a second input coupled to receive a transmit mode signal, and third and fourth outputs for outputting transmit/receive switch control signals to a respective one of said high-voltage transmit/receive switches for controlling the state of said high-voltage transmit/receive switch, said transmit/receive switch control signals being a function of said low-voltage pulser control signals and said transmit mode signal.

14. The probe as recited in claim 10, further comprising a multiplicity of low-voltage ground switches, each of said low-voltage ground switches being disposed between ground and a respective one of said high-voltage transmit/receive switches for allowing its output to float when said low-voltage ground switch is off and said respective one of said high-voltage transmit/receive switches is on, each of said low-voltage ground switches providing a low-impedance path to ground during the transmit cycle so that the respective transducer can be discharged to ground whenever the respective transmit/receive switch turns on.

15. The probe as recited in claim 10, further comprising a multiplicity of low-voltage pulsers, each of said low-voltage pulsers being protected from a respective one of said high-voltage pulsers by a respective one of said high-voltage transmit/receive switches.

16. The probe as recited in claim 10, wherein each of said ultrasonic transducers comprises a respective multiplicity of micromachined ultrasonic transducer cells that are interconnected and not switchably disconnectable from each other.

17. The probe as recited in claim 10, wherein said ultrasonic transducers and said high-voltage transmit/receive switches are incorporated in a head of said probe, further comprising pulse timing circuitry incorporated in a handle of said probe.

18. An integrated device comprising a multiplicity of ultrasonic transducers arranged along a first set of generally parallel lines in a first stratum; a multiplicity of interface circuit cells arranged along a second set of generally parallel lines in a second stratum; and a multiplicity of electrical connections, each of said electrical connections electrically connecting a respective one of said interface circuit cells to a respective ultrasonic transducer, wherein each of said interface circuit cells comprises: a high-voltage pulser for driving the respective ultrasonic transducer, a low-voltage switch for providing pulser control signals when said switch is on, a low-voltage digital control circuit that outputs switch state control signals for controlling the state of said low-voltage switch, and a high-voltage transmit/receive switch disposed between said low-voltage switch and the respective ultrasound transducer for providing a path for receive signals from the respective ultrasound transducer to said low-voltage switch when said transmit/receive switch is on, wherein said transmit/receive switch blocks the pulser output from reaching said low-voltage switch via said path when said transmit/receive switch is off, and a low voltage splitter having a first input coupled to receive pulser control signals passed through said low-voltage switch, and an output in electrical connection with said high-voltage pulser.

19. The device as recited in claim 16, wherein said splitter is configured to separate said pulser control signals into a positive cycle pulser control signal and a negative cycle pulser control signal that are sent from first and second outputs respectively, said pulser comprising respective inputs for receiving said positive and negative cycle pulser control signals.

20. The device as recited in claim 19, wherein said splitter has a second input coupled to receive a transmit mode signal, and third and fourth outputs for outputting transmit/receive switch control signals to said transmit/receive switch for controlling the state of said transmit/receive switch, said transmit/receive switch control signals being a function of said pulser control signals and said transmit mode signal.

21. The device as recited in claim 18, wherein each of said interface circuit cells further comprises a low-voltage ground switch disposed between ground and said transmit/receive switch for allowing said path to float when said ground switch is off and said transmit/receive switch is on, said low-voltage ground switch providing a low-impedance path to ground during the transmit cycle so that the transducer can be discharged to ground whenever the transmit/receive switch turns on.

22. The device as recited in claim 18, wherein each of said interface circuit cells further comprises a respective low-voltage pulser that is protected from said high-voltage pulser by said transmit/receive switch.

23. The device as recited in claim 18, wherein each of said ultrasonic transducers comprises a respective multiplicity of micromachined ultrasonic transducer cells that are electrically interconnected and not switchably disconnectable from each other.

24. An ultrasound transducer array comprising a multiplicity of ultrasound transducers, a multiplicity of interface circuit cells, and a multiplicity of output nodes, each interface circuit cell being electrically connected to a respective one of said ultrasound transducers via a respective one of said output nodes, wherein each of said interface circuit cells comprises: a high-voltage pulser for driving the respective ultrasound transducer, a low-voltage switch for providing pulser control signals when said low-voltage switch is on, a low-voltage digital control circuit that outputs switch state control signals for controlling the state of said low-voltage switch, and a high-voltage transmit/receive switch disposed between said low-voltage switch and the respective ultrasound transducer for providing a path for receive signals from the respective ultrasound transducer to said low-voltage switch when said transmit/receive switch is on, wherein said transmit/receive switch blocks the pulser output from reaching said low-voltage switch via said path when said transmit/receive switch is off, and a low voltage splitter having a first input coupled to receive pulser control signals passed through said low-voltage switch, and an output in electrical connection with said high-voltage pulser.

25. The ultrasound transducer array as recited in claim 24, wherein each of said ultrasound transducers comprises a respective multiplicity of micromachined ultrasonic transducer cells that are electrically interconnected and not switchably disconnectable from each other.

26. An ultrasound transducer probe comprising a plurality of integrated devices tiled together in two rows, wherein each of said integrated devices has four sides and comprises: a multiplicity of ultrasonic transducers arranged along a first set of generally parallel lines disposed in an area of a first stratum; a multiplicity of interface circuit cells arranged along a second set of generally parallel lines disposed in a first area of a second stratum that underlies said area of said first stratum; a first multiplicity of electrical connections, each of said electrical connections of said first multiplicity electrically connecting a respective one of said interface circuit cells to a respective ultrasonic transducer; a multiplicity of pads disposed in a second area of said second stratum that does not overlap with said first area of said second stratum and extends along a marginal area extending along one of said four sides; and a second multiplicity of electrical connections, each of said electrical connections of said second multiplicity electrically connecting a respective one of said interface circuit cells to a respective pad, wherein each of said interface circuit cells comprises: a high-voltage pulser for driving the respective ultrasonic transducer, a low-voltage switch for providing pulser control signals when said switch is on, a low-voltage digital control circuit that outputs switch state control signals for controlling the state of said low-voltage switch, and a high-voltage transmit/receive switch disposed between said low-voltage switch and the respective ultrasonic transducer for providing a path for receive signals from the respective ultrasonic transducer to said low-voltage switch when said transmit/receive switch is on, wherein said transmit/receive switch blocks the pulser output from reaching said low-voltage switch via said path when said transmit/receive switch is off, and a low voltage splitter having a first input coupled to receive pulser control signals passed through said low-voltage switch, and an output in electrical connection with said high-voltage pulser.

* * * * *

UNITED STATES PATENT AND TRADEMARK OFFICE
CERTIFICATE OF CORRECTION

PATENT NO.         : 7,775,979 B2                                          Page 1 of 1
APPLICATION NO. : 11/172599
DATED              : August 17, 2010
INVENTOR(S)        : Thomenius et al.

It is certified that error appears in the above-identified patent and that said Letters Patent is hereby corrected as shown below:

In Fig. 10, Sheet 9 of 21, below "INPUT" delete "/TX_ON" and insert -- TX_ON --, therefor.

In Fig. 10, Sheet 9 of 21, above Tag "102" delete "/TX_ON" and insert -- TX_ON --, therefor.

In Fig. 10, Sheet 9 of 21, below Tag "94" delete "/TX_ON" and insert -- TX_ON --, therefor.

In Fig. 24, Sheet 20 of 21, for Tag "61", in Line 1, delete "TRANSIT" and insert -- TRANSMIT --, therefor.

In Fig. 25, Sheet 21 of 21, for Tag "61", in Line 1, delete "TRANSIT" and insert -- TRANSMIT --, therefor.

In Column 6, Line 26, delete "pursers" and insert -- pulsers --, therefor.

In Column 13, Line 25, delete "(FETS)" and insert -- (FETs) --, therefor.

In Column 22, Line 7, in Claim 19, delete "claim 16," and insert -- claim 18, --, therefor.

Signed and Sealed this

Twelfth Day of October, 2010

David J. Kappos
*Director of the United States Patent and Trademark Office*